United States Patent
Mikhaiel et al.

(10) Patent No.: US 12,298,296 B2
(45) Date of Patent: May 13, 2025

(54) METHODS AND DEVICES FOR SEPARATION OF BLOOD COMPONENTS

(71) Applicant: Canon Virginia, Inc., Newport News, VA (US)

(72) Inventors: Nabil Mikhaiel, Newport News, VA (US); Lindsay Sanford, Coventry, CT (US); Kelly Coughenour, Newport News, VA (US); Jeremy Schreiber, Newport News, VA (US)

(73) Assignee: Canon Virginia, Inc., Newport News, VA (US)

( * ) Notice: Subject to any disclaimer, the term of this patent is extended or adjusted under 35 U.S.C. 154(b) by 0 days.

(21) Appl. No.: 17/929,203

(22) Filed: Sep. 1, 2022

(65) Prior Publication Data

US 2023/0030206 A1     Feb. 2, 2023

Related U.S. Application Data

(62) Division of application No. 16/203,336, filed on Nov. 28, 2018, now Pat. No. 11,448,641.

(Continued)

(51) Int. Cl.
    *G01N 33/50*         (2006.01)
    *A61M 1/02*          (2006.01)

(Continued)

(52) U.S. Cl.
    CPC ....... *G01N 33/5002* (2013.01); *A61M 1/0259* (2013.01); *A61M 1/029* (2013.01);

(Continued)

(58) Field of Classification Search
CPC ........ G01N 33/5002; G01N 1/18; G01N 1/40; G01N 1/4077; G01N 2001/4083; G01N 15/04; G01N 15/042; G01N 15/05; G01N 1/4005; G01N 2001/4088; G01N 15/025; G01N 15/045; G01N 15/075; G01N 15/14; G01N 15/1429; G01N 15/1432; G01N 15/1434; G01N 21/01; G01N 2021/0118; G01N 2021/0125; A61M 1/029; A61M 1/0259; A61M 2202/0415; A61M 1/025; B04B 5/0442; B04B 13/00; B04B 5/0414; B01D 17/0208; B01D 17/0214; B01D 17/0217; B01D 17/045; B01D 17/047; B01D 17/048; B01D 21/01; B01D 21/26; B01D 21/262; B01D 21/28; B01D 21/286; B01D 2221/10; C12N 15/10; C12N 15/1003; C12M 33/08; C12M 33/10; C12M 33/22; C12M 45/20; C12M 47/10;

(Continued)

(56) References Cited

U.S. PATENT DOCUMENTS 5,605,842 A *   2/1997   Langley ................ A61M 1/385
                                                                        436/63
5,607,579 A *   3/1997   Latham, Jr. ......... A61M 1/3693
                                                                        494/35

(Continued)

*Primary Examiner* — Joseph W Drodge
(74) *Attorney, Agent, or Firm* — Rothwell, Figg, Ernst & Manbeck, P.C.

(57) ABSTRACT

The present disclosure relates to methods and devices for the separation of blood components including separation by rapid sedimentation, including in an automated fashion.

11 Claims, 23 Drawing Sheets
(23 of 23 Drawing Sheet(s) Filed in Color)

Related U.S. Application Data

(60) Provisional application No. 62/591,761, filed on Nov. 28, 2017.

(51) Int. Cl.
  B01D 17/02 (2006.01)
  B01D 21/28 (2006.01)
  B01L 3/00 (2006.01)
  B04B 5/04 (2006.01)
  B04B 13/00 (2006.01)

(52) U.S. Cl.
  CPC ....... B01D 17/0214 (2013.01); B01D 21/286 (2013.01); B01L 3/523 (2013.01); B04B 5/0442 (2013.01); B04B 13/00 (2013.01); *A61M 2202/0415* (2013.01); *B01L 2300/0672* (2013.01)

(58) Field of Classification Search
  CPC . C12M 47/12; C12Q 1/24; C12Q 1/68; B01L 3/523; B01L 3/563; B01L 2300/0672
  See application file for complete search history.

(56) References Cited

U.S. PATENT DOCUMENTS

| | | | |
|---|---|---|---|
| 6,336,358 B1* | 1/2002 | Kishimori | G01N 15/042 73/61.65 |
| 9,244,065 B1* | 1/2016 | Schaff | G01N 33/543 |
| 9,554,422 B2 | 1/2017 | Coursey et al. | |
| 9,795,961 B1* | 10/2017 | Koh | G01N 15/04 |
| 11,448,641 B2* | 9/2022 | Mikhaiel | B04B 13/00 |
| 2002/0084215 A1* | 7/2002 | Coville | B01D 61/147 422/534 |
| 2002/0160523 A1* | 10/2002 | Wyant | G01N 15/1468 435/7.1 |
| 2003/0022382 A1 | 1/2003 | Negersmith | |
| 2005/0051466 A1* | 3/2005 | Carter | G01N 15/05 210/512.1 |
| 2005/0175798 A1 | 8/2005 | Kurokawa et al. | |
| 2005/0233460 A1* | 10/2005 | Clague | G01N 11/162 422/68.1 |
| 2008/0045394 A1* | 2/2008 | Kolenbrander | B04B 15/00 494/7 |
| 2008/0153078 A1 | 6/2008 | Braman et al. | |
| 2008/0172023 A1* | 7/2008 | Thompson | G01N 30/24 604/411 |
| 2009/0291818 A1* | 11/2009 | Soares | B01L 3/50215 494/37 |
| 2010/0025336 A1* | 2/2010 | Carter | G01N 15/05 210/740 |
| 2010/0078392 A1* | 4/2010 | Sweat | G01N 15/042 210/745 |
| 2010/0151438 A1* | 6/2010 | Yu | G01N 33/491 435/2 |
| 2010/0184228 A1 | 7/2010 | Saiki | |
| 2011/0076668 A1 | 3/2011 | Oguro | |
| 2012/0111127 A1* | 5/2012 | Maeda | G01N 35/1097 73/863.01 |
| 2012/0164644 A1* | 6/2012 | Neely | G01R 33/302 435/6.15 |
| 2013/0059288 A1 | 3/2013 | Dankbar et al. | |
| 2014/0154733 A1* | 6/2014 | Sacchetti | G01N 33/4915 435/29 |
| 2014/0178251 A1* | 6/2014 | Yamada | G01N 35/0099 422/67 |
| 2016/0186165 A1* | 6/2016 | Dose | B03C 1/01 435/173.9 |
| 2017/0043336 A1* | 2/2017 | Khattak | G01N 35/00029 |
| 2017/0120234 A1* | 5/2017 | Hofmann | B01L 9/54 |
| 2017/0325288 A1 | 11/2017 | Coursey et al. | |
| 2018/0136194 A1* | 5/2018 | Sinn Blandy | G01N 33/491 |
| 2018/0196031 A1* | 7/2018 | Carew | A61D 1/00 |
| 2018/0296748 A1* | 10/2018 | Emerson | A61J 1/2072 |
| 2019/0265265 A1* | 8/2019 | Yamada | G01N 35/1002 |
| 2019/0381501 A1* | 12/2019 | Wang | G01N 35/1079 |

* cited by examiner

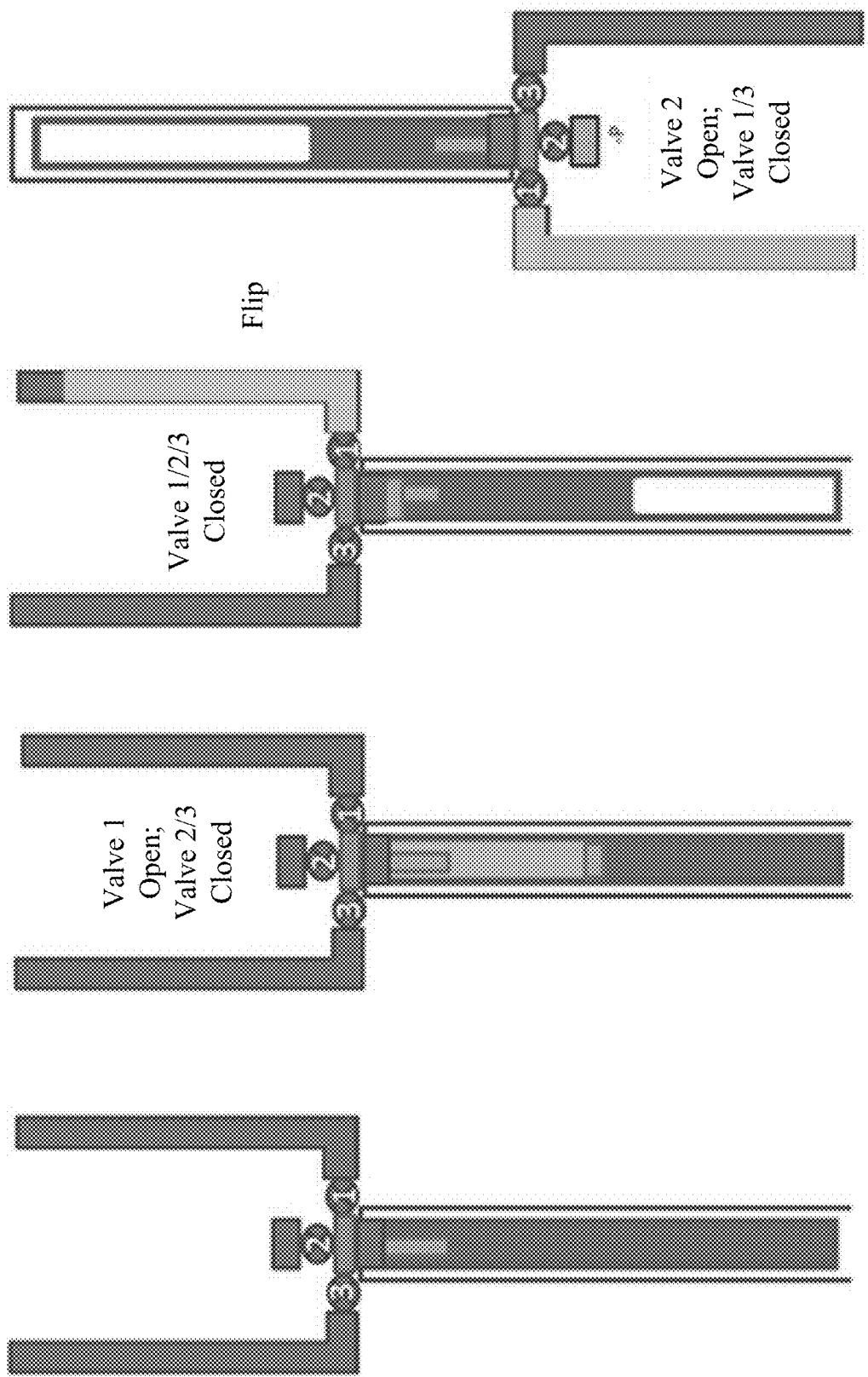

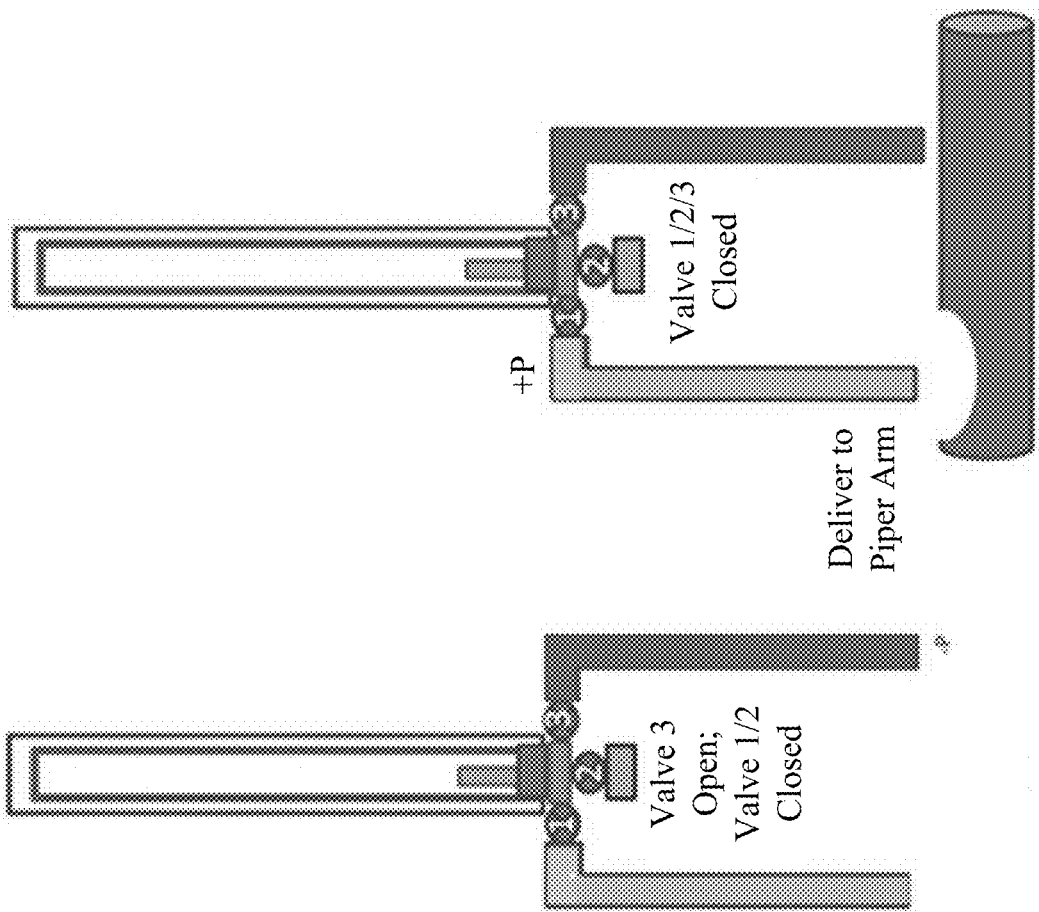

FIG. 12A

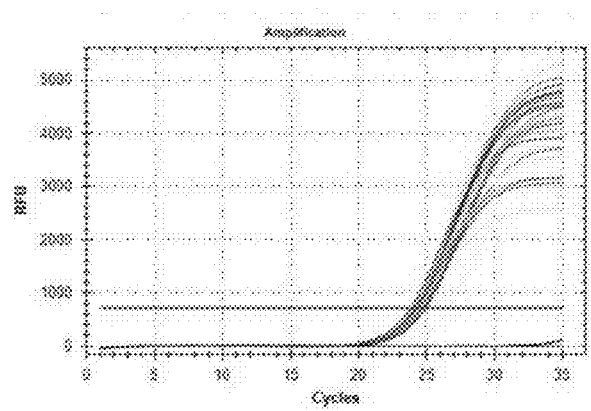

FIG. 12B

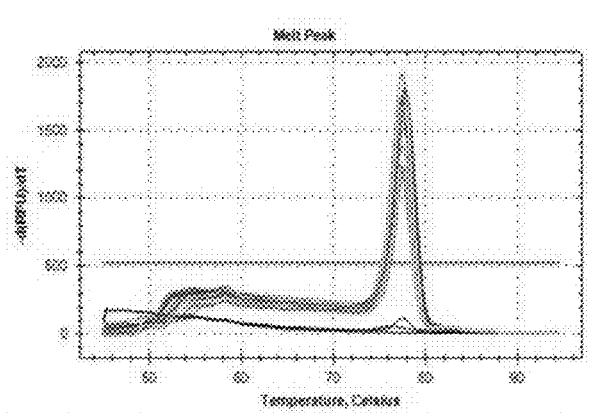

| Aggregate | Color | Average Cq | Standard Dev. |
|---|---|---|---|
| PEG 35 mg/mL + SC | Yellow | 25.1 | 1.3 |
| PEG 35 mg/mL + H2O | Light green | 24.4 | 0.3 |
| Fibrinogen 25 mg/mL + H2O | Red | 24.5 | 0.4 |
| Fibrinogen 25 mg/mL + SC | Light blue | 24.3 | 0.3 |
| Fibrinogen 15 mg/mL + SC | Pink | 24.6 | 0.2 |
| Fibrinogen 15 mg/mL + H2O | Dark purple | 24.2 | 0.1 |
| Dextran 25 mg/mL + SC | Orange | 24.1 | 0.1 |
| Dextran 25 mg/mL + H2O | Blue | 24.2 | 0.3 |
| WB + SC Control | Brown | 24.5 | 0.3 |
| WB only Control | Teal | 24.4 | 0.1 |
| Positive Control (DNA) | Dark green | 24.5 | 0.4 |
| Negative Control (DNA) | Black | N/A | N/A |

METHODS AND DEVICES FOR SEPARATION OF BLOOD COMPONENTS

CROSS-REFERENCE TO RELATED APPLICATION

The present application a divisional of U.S. Ser. No. 16/203,336, filed Nov. 28, 2018, which claims the benefit of priority to U.S. Provisional Application Ser. No. 62/591,761 filed Nov. 28, 2017, which is incorporated herein by reference in their entireties.

FIELD OF THE DISCLOSURE

The present application relates to methods and devices to fractionate blood components including separation by rapid sedimentation, and optionally in an automated fashion. These methods and devices can be used in isolating circulating cell-free DNA (ccfDNA). The methods and devices purify, extract and/or quantify ccfDNA concentration levels from plasma. In addition to the separation of plasma from whole blood, this application is additionally applicable to the separation of additional components/layers (such as the buffy coat) and cellular populations.

Plasma makes up about 55% of the body's total blood volume and it is mostly water (up to 95% by volume), and contains dissolved proteins, glucose, clotting factors, electrolytes, hormones, gases and circulating nucleic acids. Therefore, an efficient blood plasma separation step is required to achieve the intended workflow of a diagnostic system. While the methods and systems provided here have the potential to be integrated into a full diagnostic system, they also have the capacity to function as a standalone method and/or device to achieve efficient plasma separation from whole blood.

BACKGROUND OF THE DISCLOSURE

Human plasma is an important and convenient source of circulating biomarkers. The quality of biomarkers often depends not only on biological factors such as physical condition and age of the patient, but also on technical factors such as the lack of standardization of sample collection and preparation. Amongst other technical factors, in vitro hemolysis (the rupture or destruction of red blood cells), is a well-known source of biomarker variability. Blood cells such as leukocytes, or white blood cells, can also be a source of contamination in relation to biomarkers such as circulating cell-free DNA (ccfDNA) targets. Therefore, plasma separation from blood cells is very desirable in most cases. Ideal separation is achieved with the least amount of hemolysis, highest plasma yield and efficiency, and in a time suitable to meet the needs of the specific application. Here plasma yield is defined as the volume of plasma separated from whole blood and efficiency is defined as the purity of the plasma.

Many molecular diagnostics processes and applications, particularly those involving ccfDNA, require purified plasma from whole blood as the starting material. While automated systems exist to support analyte isolation and downstream processing, these systems often utilize plasma as the starting input material, with the step of extracting plasma from whole blood omitted as part of the automated workflow, and the burden of performing the extraction placed on the user during a manual processing step. A typical processing step involves low speed centrifugation of blood collection tubes to pellet the cells, leaving the plasma as a separate layer on top of the cells. However, this step does require access to a centrifuge, adds to the time required, and can present additional biohazardous exposure. This manual process is burdensome, time consuming, and provides multiple routes of pre-analytic variation that can arise from different centrifugation regimes, user aptitude in pipetting off different blood component layers, etc. Even skilled and technically proficient users may struggle in manually removing blood component layers, particularly the buffy coat, which exists as a key source of genomic DNA contamination in ccfDNA isolation from plasma. As such, an automated solution to extract plasma from whole blood would meet a key user need and help to protect the user from exposure to potentially infectious material, something that is of significant benefit particularly in point of care (POC) applications. Furthermore, a non-centrifugation based method of plasma separation that could support a wide range of input volumes would be particularly advantageous in meeting the demands of a variety of applications.

Many diagnostic device manufacturers have tried to solve the problem of automated blood processing. From a technical perspective, in order to meet a growing demand for robust point of care (POC) diagnostics, specific requirements must be met. These requirements include equipment that is limited in terms of size and cost, of which centrifugation is a poorly suited match. However, some manufacturers have incorporated centrifugal separation mechanics into their instruments. Not only does the centrifugal mechanics add considerable complexity to the system, it also adds substantial size to the instrument and may require an additional expensive disposable plastic accessory. Some manufacturers have developed lateral flow devices which incorporate layers of absorbent and membrane materials that serve to retard blood cells and wick the plasma along a substrate layer to a detection zone. These devices don't achieve true plasma separation but rather take advantage of the size of cells to slow their progress in lateral flow relative to the plasma. These devices, although easy to use while producing rapid results, are generally not very quantitative or sensitive and therefore lack clinical utility in many situations. In addition, they all share a risk of hemolysis due to applying some sort of direct shear stress on blood cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated herein and form part of the specification, illustrate various embodiments of the present disclosure.

FIG. 3A shows a tube containing blood post-centrifugation with oil in a tilted position. FIG. 3B shows the tube in a horizontal position with the plasma pinched off from the remaining blood components and fully surrounded by oil. FIG. 3C shows the variation in pinch placement based on oil volume.

FIGS. 9A-9F are a workflow for the device of FIG. 7.

FIGS. 12A-12C provide graphs and a table showing qPCR and thermal melting results.

FIG. 15 is a photograph of visual analysis software monitoring separation of blood samples.

FIG. 23 is a table showing filtration test results.

FIG. 24 is a table showing filtration test results.

DEFINITIONS

Figure 1:
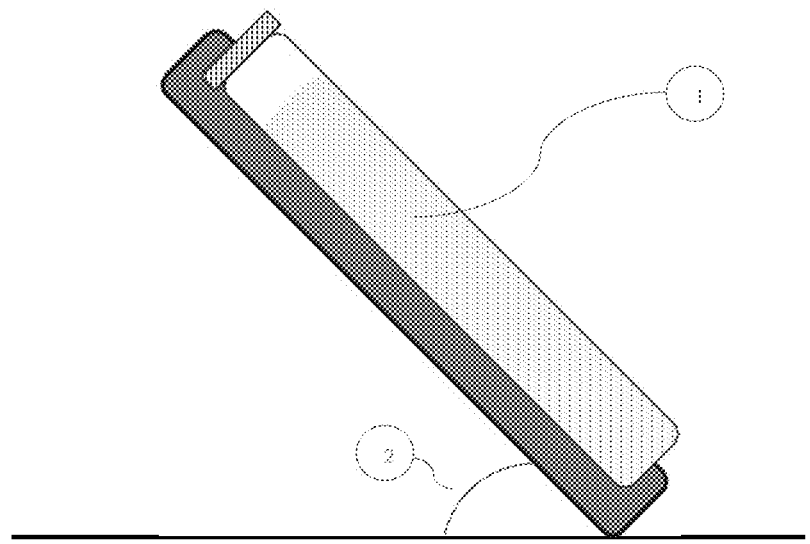
FIG. 1 is a diagram depicting a sample vessel (1) inclined at an angle (2).

Aggregation: the reversible clumping of red blood cells under low shear forces or at stasis. Erythrocytes aggregate in a special way, forming rouleaux. Rouleaux formation takes place only in suspensions of RBC containing high molecular, fibrillar proteins or polymers in the suspending medium.

Centrifugal Force: An outward force on a body that is rotating around an axis.

Centrifugation: Achieved by rotating (spinning) samples at a high speed, thus enabling separation of substances with different densities via centrifugal force.

Coagulation: also known as clotting, is the process by which blood changes from a liquid to a gel or solid, forming a blood clot. The mechanism of coagulation involves activation, adhesion, and aggregation of platelets along with deposition and maturation of fibrin.

Erythrocytes: Most common type of blood cell, accounting for 98% of blood cells, at a concentration of 5 million per uL of blood. Responsible for the transport of oxygen in blood. Erythrocytes are 3-5 um large and have a discoid shape. Also known as red blood cells (RBCs).

Erythrocyte Sedimentation Rate (ESR): Erythrocyte sedimentation rate is the rate at which red blood cells sediment in a period of one hour. It is a common hematology test, and is a non-specific measure of inflammation.

Hematocrit: Volume percentage of RBCs in blood. This value depends on the age and health of the patient. Approximated at 40-50% for healthy patients Leukocytes: Account for 1% of the total blood cells, at a concentration of 4-10 thousand per uL of blood, with sizes varying from 7 to 30 um. Leukocytes play a major role in the immune response. Also known as white blood cells (WBCs).

Plasma: Liquid phase of the blood. Supernatant collected after centrifugation of a blood sample in which anticoagulant was added. Plasma contains fibrinogen and other clotting proteins.

Plasmaphoresis: An in vivo process used for treatment of different conditions including autoimmune disorders. In this process plasma is separated from blood cells or undergoes treatment before being returned to the body. This term can also be in reference to plasma donation (in this case the plasma is reserved for treatment purposes and the blood cells are returned to the donor).

Purity: Purity relates to the number of RBCs remaining in the plasma extracted. In this review it is defined as a percentage by: $1-Cp/Cf$ Where $Cp$ is the number of RBCs in the plasma fraction and $Cf$ is the number of RBCs in the feed (inlet) fraction; e.g.: 100% purity means no cells were detected in the plasma fraction.

Serum: Supernatant collected after centrifugation of a blood sample in which no anticoagulant was added.

Yield: The percentage of extracted plasma volume over the total volume of blood injected.

DETAILED DESCRIPTION

The present disclosure has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

The practice of the present disclosure may employ, unless otherwise indicated, conventional techniques and descriptions of clinical chemistry, molecular biology (including recombinant techniques), cell biology, biochemistry, and immunology, which are within the skill of the art.

Several studies have showed a correlation between elevated levels of fibrinogen or other large plasma proteins and enhanced red blood cell (RBC) aggregation. In addition, the effects of molecular mass and concentration for neutral polymers (macromolecules) such as dextran on RBC aggregation are well documented in literature (Neu, B. et al. (2001). Aggregation of human RBC in binary dextran-PEG polymer mixtures. Biorheology, 38(1), 53-68; Suzuki, Y. et al. (2001). Aggregation and sedimentation of mixtures of erythrocytes with different properties. Clinical Hemorheology and Microcirculation, 25(3-4), 105-17; Pribush, A. et al. (2007). The mechanism of the dextran-induced red blood cell aggregation. European Biophysics Journal, 36(2), 85-94; Neu, B. et al. (2008). Effects of dextran molecular weight on red blood cell aggregation. Biophysical Journal, 95(6), 3059-65). Aggregated blood cells have a higher sedimentation rate compared to single cells due to their increased mass and density. Another factor that has effect on the sedimentation rate of RBCs is the degree of inclination of the housing tube. One study shows that if a standard test tube deviates as little as 5 degrees from the vertical it can cause the observed sedimentation rates to double relative to a vertical tube (O'Nrien R. et al. (1973). Erythrocyte Sedimentation Rates in Inclined Vessels, Can. J. Physiol. Pharmacol 685-690).

This disclosure is focused on fractionating blood components. The components can be separated by rapid sedimentation, including in an automated fashion. Rapid sedimentation can be caused by the introduction of an aggregation agent, or by introducing the sample to a physical or mechanical aggregation means. While the initial primary focus is the separation of plasma from whole blood, the disclosure can also address separation of additional components/layers (such as the buffy coat) and cellular populations as well.

Unstirred suspensions of erythrocytes (red blood cells) form stable spherical aggregates of uniform size. The radius of the spheres depends upon the suspending medium and the hematocrit (the ratio of the volume of red blood cells to the total volume of blood). Erythrocyte suspensions will undergo sedimentation only after these aggregates are formed. Aggregation is a two-step process: first, erythrocytes associate in long chains or clumps that resemble a stack of coins, which are called rouleaux. Next, these chains form clusters of uniform size. The requirements for this well-defined process are: 1. an electrolyte, 2. neutral or negatively charged macromolecules in a solution and 3. a metabolically active red blood cell. Once the clusters of uniform size are formed the sedimentation will start at a rate dependent on the size of the clusters. Large cluster fall faster than small ones, so factors that increase aggregation will increase sedimentation. Sedimentation concludes with the packing stage, wherein the rate of sedimentation approaches zero, and cells start to pack in the bottom of the vessel.

The present disclosure is therefore based on sedimentation replacing the need for centrifugation to achieve component separation and automated fractionation replacing the need for manually separating component layers, thus meeting two key needs for applications focused in POC settings.

The disclosure provided includes a method for efficiently separating blood components using aggregation agents to enhance blood cell aggregation. Separation can be achieved by mixing whole blood with a solution containing various concentrations of an aggregation agent, for example, a particular molecular mass fraction of protein or polymer (such as fibrinogen or dextran) to induce red blood cell aggregation and incubating the whole blood and aggregation agent mixture to accelerate the sedimentation rate of the RBCs. Within the present disclosure, all of the provided embodiments accelerate the separation of whole blood into blood components. Within this context, accelerate means that the separation into blood components occurs at a faster rate than would occur if the sample or whole blood remained untouched and stationary for a period of time, usually up to an hour. In some embodiments, the whole blood and aggregation agent mixture can additionally be subjected to a mechanical or physical aggregation means, including, without limitation, inclining the vessel containing the mixture, exposing the vessel to one or more of vibration, heating, tapping, and an electromagnetic field.

Aggregation Agents

The present disclosure includes the use of an aggregation agent that can be added to a sample containing whole blood for the purpose of causing RBCs in the sample to aggregate and undergo sedimentation to allow for separation of the blood components. Aggregation agents refers to an additive that may bind, aggregate, adhere, agglutinate or form a complex with a desired cell type, for example, RBCs. An aggregation agent can also refer to an additive that may cause a desired cell type, for example RBCs, to bind, aggregate, adhere, agglutinate, or form a complex with like or different cell types. Aggregation agents may accomplish cell aggregation by activating natural biochemical pathways, by altering cell mechanics, or by changing the physical environment of the sample.

In one embodiment, aggregation agents can include acute phase proteins or other macromolecules. Acute phase proteins are proteins whose plasma concentrations increase or decrease in response to inflammation. For example, acute phase proteins can include C-reactive protein, Serum amyloid P component, Serum amyloid A, Complement factors, Mannan-binding lectin, Fibrinogen, prothrombin, factor VIII, von Willebrand factor, Plasminogen activator inhibitor-1 (PAI-1), Alpha 2-macroglobulin, Ferritin, Hepcidin, Ceruloplasmin, Haptoglobin, Orosomucoid, Alpha-1-acid glycoprotein, Alpha 1-antitrypsin, Alpha 1-antichymotrypsin, albumin, transferrin, transthyretin, retinol-binding protein, antithrombin, and transcortin, In another embodiment, aggregation agents can include Fibrinogen, Dextran, Hydroxyethyl Starch (HES), Polyvinylpyyrolidone (PVP), Polyethylene Glycol (PEG), and Gelatin. In another embodiment, aggregation agents can include Dextran having a molecular weight of 70K or 150K.

In a further embodiment, aggregation agents can be added to a sample at a concentration of about 5 to about 125 mg/ml. In another embodiment, the aggregation agents can be used at a concentration of about 5 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 60 mg/ml, about 70 mg/ml, about 80 mg/ml, about 90 mg/ml, about 100 mg/ml, about 110 mg/ml, about 120 mg/ml, about 130 mg/ml, about 140 mg/ml or about 150 mg/ml.

Inclined Sedimentation

Inclined tubes can be used to increase sedimentation flow rates and achieve velocities many times greater than the single-particle terminal settling velocity, by increasing the available settling area. In one embodiment, the vessel containing the blood and aggregation agent mixture can be incubated while placed in an inclined position. In some embodiments, the inclined position can be from 2 to 60 degrees from a vertical position, as shown in FIG. 1. In another embodiment, the inclined position can be from 5 to 60 degrees, from 10 to 60 degrees, from 20 to 60 degrees, from 40 to 60 degrees, from 45 to 60 degrees, or from 50-60 degrees from a vertical position. In some embodiments, the inclined position can be 2, 3, 5, 10, 15, 20, 25, 30, 25, 40, 45, 50, 55, or 60 degrees from vertical.

Vessel Geometry

Figure 2:
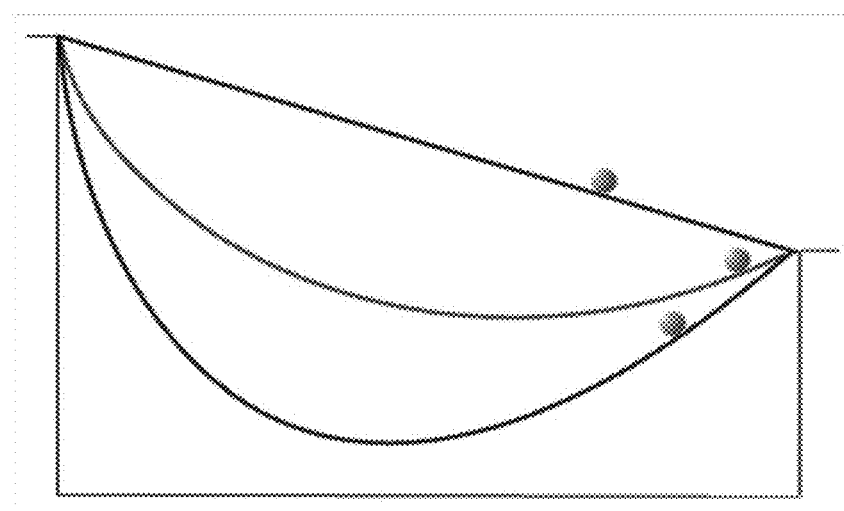
FIG. 2 is a diagram showing a brachistochrone curve.

It may be possible to further still increase the sedimentation based on the geometry of a rolling object (erythrocytes on a surface). Due to gravity, the shortest route between two points such that the route takes the least amount of time to travel from point A to point B, where the two points are at different elevations, then due to gravity, the shortest route is the brachistochrone curve, as shown in FIG. 2. In FIG. 2, the middle brachistochrone (inverted cycloid) curve is the curve of fastest descent between two points. In mathematics and physics, a brachistochrone curve is "the one lying on plane between a point A and a lower point B, where B is not directly below A, on which a bead slides under the influence of a uniform gravitational field to a given end point in the shortest time". A Brachistochrone curve is a specific form of cycloids, and is an example of a roulette, a curve generated by a curve rolling on another curve.

Thus, it is an embodiment of the present disclosure that the vessel containing the blood and aggregation agent mixture can be a vessel having a brachistochrone curve geometry. In one embodiment, the vessel can be a cylindrical tube having a brachistochrone curve geometry.

Tapping/Vibration

Another embodiment to increase the sedimentation rate and/or to release RBCs adhered to the side wall is to apply a mechanical aggregation means to the vessel containing the blood and aggregation agent mixture by applying continuous or discrete intervals of tapping on the vessel. In one embodiment, this tapping force can be created by an automated system. In one embodiment, the tapping is applied a discrete number of times during incubation, for example, 5, 10, 15, 20, 25, 30, 35, 40, 45, 50 or more times. In another embodiment, the tapping is applied 10-20 times. In a further embodiment, the tapping can be applied over the entire length of the incubation period, or the tapping can be applied over a subset of the incubation period, for example, over 1-20 minutes, over 1-10 minutes, over 1-5 minutes, or over 1-2 minutes.

In another embodiment, vibration can be applied to the vessel in order to create turbulent flow that will increase the sedimentation rate and/or to release RBCs adhered to the side wall. This can be done, for example, by attaching the vessel to a micro size vibration motor with a controller to control the vibration speed and duration.

Sample Dilution/Heating

At terminal (or settling) velocity, the excess force Fg due to the difference between the weight and buoyancy of the sphere (both caused by gravity) is given by:

$$v = \frac{2}{9}\frac{(\rho_p - \rho_f)}{\mu}gR^2$$

where:
g is the gravitational acceleration (m/s$^2$);
R is the radius of the spherical particle;
$\rho_p$ is the mass density of the particles (kg/m$^3$);
$\rho_f$ is the mass density of the fluid (kg/m$^3$); and
$\mu$ is the dynamic viscosity (kg/m*s).

From this equation, the only variables that can be changed to achieve faster settling velocity are the fluid density (plasma) and the dynamic viscosity. Therefore, by lowering the plasma density and viscosity, a faster sedimentation rate can be achieved. An embodiment of the disclosure is that a reduced fluid viscosity can be attained by diluting the blood sample, for instance, in PBS, phosphate-buffered saline. Different dilution ratios can be used depending on the final desired analyte concentration.

Figure 3A:
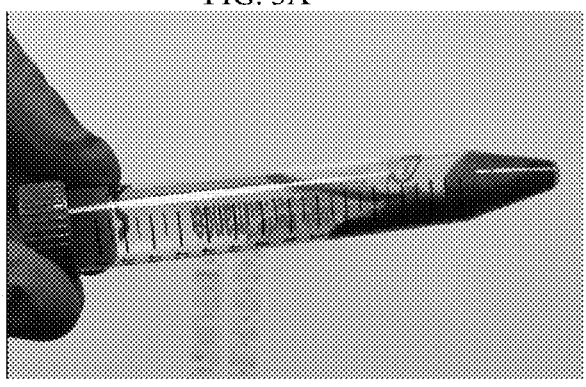
FIGS. 3A-3C are photographs depicting the oil pinching process.
Figure 3B:
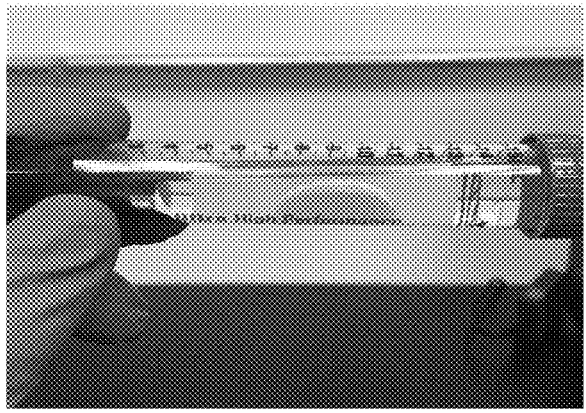

Another embodiment of the disclosure is a method to lower the fluid viscosity by increasing the sample temperature. A fluid's viscosity strongly depends on its temperature such that the higher the temperature is, the lower a substance's viscosity is. Consequently, decreasing temperature causes an increase in viscosity. The relationship between temperature and viscosity is inversely proportional for all substances. Plasma is a Newtonian fluid; its viscosity is independent of blood flow characteristics, but is determined basically by water content and macromolecular components of blood. Typical values for the viscosities of normal human plasma and serum, at 37° C., are 1.2 and 1.1 mN s m-2. The viscosity of normal plasma varies with temperature in just the same way as does that of its solvent, water. A 5° C. increase of temperature reduces plasma viscosity by about 10%, see FIGS. 3A-3C.

A study on thermal instability of red blood cells (Gershfeld and Murayama 1988) showed that at temperatures equal to or less than 37° C. no hemolysis was observed, while for temperatures exceeding 45° C. hemolysis rates are rapid and are accompanied by gross changes in cellular morphology. Therefore, using temperature as a method to accelerate sedimentation rate will be limited to temperatures less than 37° C. in order to avoid hemolysis. Accordingly, an embodiment of the present disclosure is to increase the rate of sedimentation of a blood and aggregation agent mixture by increasing the temperature of the mixture between 1 and 25° C., or between 2 and 20° C., or between 3 and 10° C., or about 5° C.

Electromagnetic Fields

Studies have reported the harmful effects of electromagnetic fields generated from electric, electronic, and wireless technologies (Havas, M. Radiation from wireless technology affects the blood, the heart, and the autonomic nervous system. Reviews on Environmental Health, 28(2-3), 75-84). These effects include clumping of the red blood cells and rouleaux formation. Havas demonstrated the increased Rouleaux between live blood (blood without any chemicals added to it) in an electromagnetically clean environment, blood from the same person after speaking on a cordless phone for 10 min, and after using a wired computer for 70 min. This same effect is leveraged in an embodiment of the present disclosure to achieve a useful application by taking advantage of the induced "big size" rouleaux formation as a method to separate plasma from blood.

In one embodiment of the disclosure, there is an apparatus and method for effectively and efficiently separating blood components wherein separation is achieved by sedimentation action via induced erythrocyte rouleaux formation and aggregation through exposure of the whole blood sample to an electromagnetic field, thus increasing the rouleaux sizes and the sedimentation rate. The plasma can then be separated from the sedimented erythrocytes by any means known to those of skill in the art, including aspirating the plasma, draining the erythrocytes to a waste container, or by a controlled shut off gate located at the blood-plasma separation phase.

Figure 4:
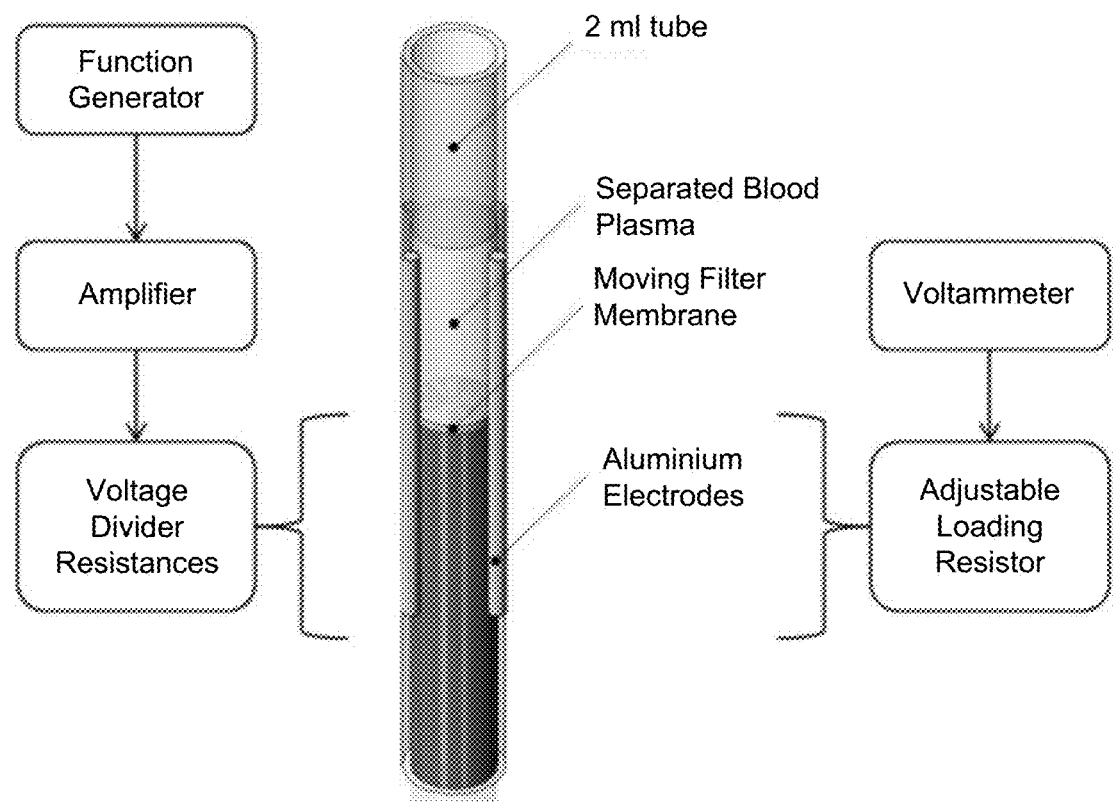
FIG. 4 is a diagram of a device for providing an electromagnetic field to a blood sample.

In a further embodiment, there is provided a device as shown in FIG. 4, which comprises two pairs of electrodes for simultaneous exposure to different field strengths. In one embodiment, the electrodes are made of any conductive metal. In a further embodiment, the electrodes are aluminum. The sample tube or vessel, made of non-conducting material (for example, PVC or glass), does not contain any metal parts that could distort the field. The length and distance between the electrodes are chosen based on the desired electric and magnetic field strength. In combined exposure to electric and magnetic fields, a loading resistor is connected to the other end of the electrodes with electric wires to a voltmeter. The electric field strength E is calculated from the voltage measured between the electrodes, and the magnetic field strength H from the current passing through the electrodes.

The voltages to the electrodes are divided by means of a series of resistors. The sinusoidal low-frequency signal is taken from a function generator and amplified with a power amplifier. The amplified signal is led to 2 pairs of electrodes attached to the sample tube or vessel holding the blood samples.

In a further embodiment, the sample tube can include a dead end filter membrane with pore size smaller than the radius of the blood cells (<3 um) that moves along the tube by, for instance, a linear actuator. The filter can move downward in the tube at a rate equal to the anticipated sedimentation rate of the blood cells controlled by active feedback control for the speed through input from optics/detection software, to filter any single cells that was not in the rouleau formations. In another embodiment, having the filter move downward from the plasma phase to the whole blood phase reduces clogging of red blood cells at the filter membrane while preventing the sedimented cells from being mixed again with the plasma.

In a further embodiment, the application of an electromagnetic field to a sample mixture ensures that no shear stress is applied directly on the blood cells, thus reducing chances of hemolysis. Other improvements of this embodiment include improved integration of plasma separation process with downstream analysis systems and well controlled plasma yield and efficiency.

Oil Pinching for Plasma Separation

Figure 5:
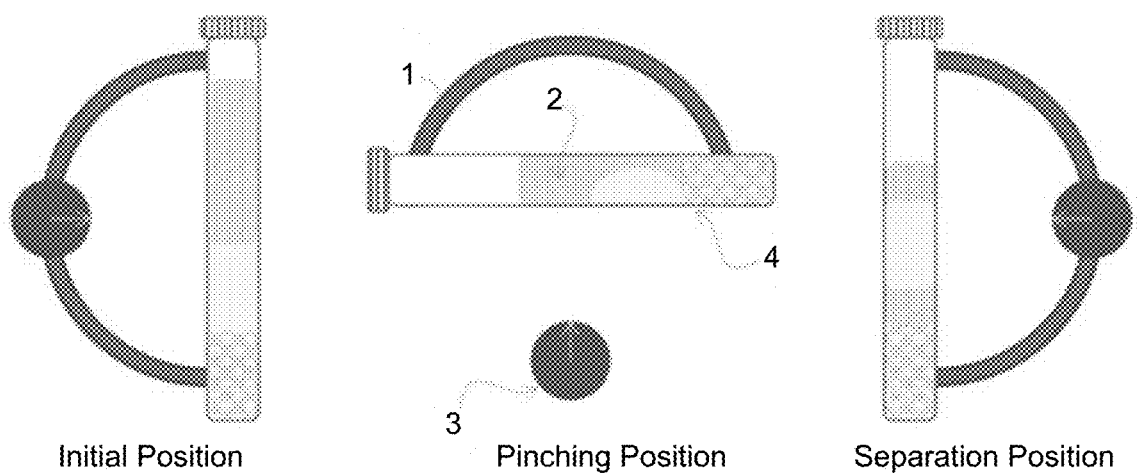
FIG. 5 is a diagram depicting the initial, pinch and separation positions of a sample vessel.

One embodiment of the present disclosure is a pipette-free method to separate blood components, including the removal of plasma from the remaining blood components. Gravitational forces along with immiscible medium can be used to create a pinch between settled blood cells and floating plasma. In one embodiment, blood vacutainer tubes are designed with specific dimensions and geometry to control the pinching mechanism. In another embodiment, an immiscible medium, for example, oil, is chosen based on the desired physical parameters including viscosity and density to achieve highest plasma yield. Once the immiscible medium is added to the sample vessel, the vessel can be tilted such that the oil in the tube surrounds at least a portion of the plasma, forming a pinch on either side of the plasma that isolates the pinched section of plasma from the remaining fluid (see FIGS. 3A and 3B). In one embodiment, the movement or tilting of the vessel can be controlled by marks on the tube to guide a user for the right angle of separation. In a further embodiment, the vessel is tilted up to 100° from vertical to perform the pinching off of the plasma, such as up to 10°, up to 20°, up to 30°, up to 40°, up to 50°, up to 60°, up to 70°, up to 80° or up to 90° from vertical. In yet a further embodiment, the vessel can be tilted more than once, including in different directions from a vertical position. In another embodiment, the process can be automated using a system that can process one or more tubes and which can tilt or rotate the one or more tubes to separate at least a portion of the plasma. FIG. 5 provides an illustration of in oil emulsification and separation of plasma in accordance with this disclosure. In FIG. 5A, the initial position of a vessel is shown where the blood components are separated into its different phases. In FIG. 5B, the tube is tilted to the pinching position, for example about 90° from vertical, and the oil creates a pinch effect between the plasma and the blood cells. In FIG. 5C, the plasma is separated and suspended in the oil ready for collection.

In another embodiment, the amount of immiscible fluid added to the vessel is optimized to ensure that the desired blood component is fully separated by the immiscible fluid without including any of the remaining components.

Automated Fractionation

Figure 6:
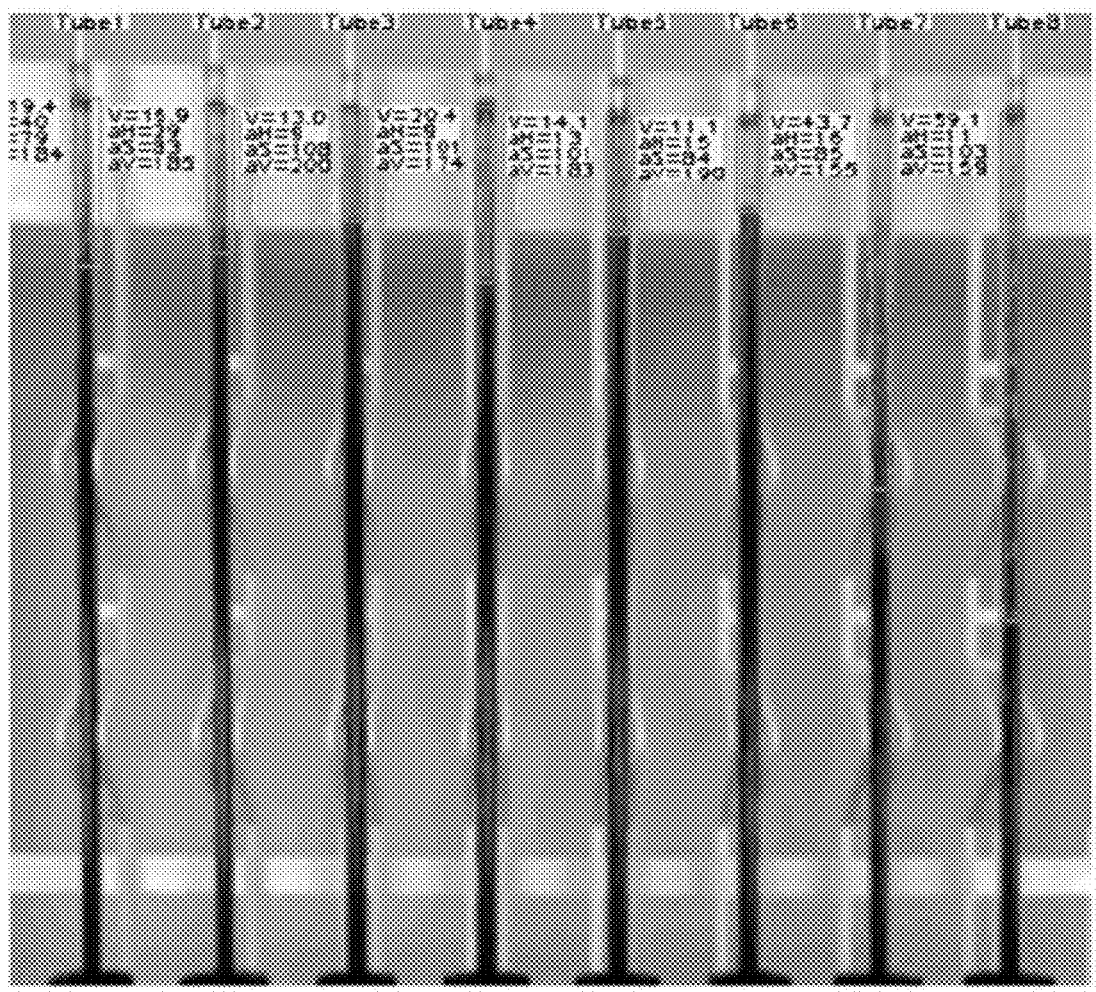
FIG. 6 is a photograph showing software tracking plasma separation of multiple vessels over time.

In another embodiment, visual processing algorithms can be used to identify and track separated blood components in a tube over time. FIG. 6 depicts software actively distinguishing and identifying the plasma/whole blood interface to actively track sedimentation rates.

In one embodiment, a system can be integrated that could automatically perform blood fractionation into at least two layers: for example, red blood cells (erythrocytes) and plasma. Algorithms can visually determine interface layers and provide active feedback to the device or system to control the amount of applied vacuum (or other similar mechanism, as is understood by one of skill in the art) which is used to siphon off each component layer into separate vessels or chambers in an automated fashion for the user.

In another embodiment, the system for automatic blood fractionation is a standalone implementation. In a further embodiment, the system integrates automated plasma separation into various sample-to-answer systems.

In one embodiment, the device is comprised of a piercing post (green) by which whole blood from a commercially available blood collection vessel or tube (such as a vacutainer containing EDTA) is interfaced. The piercing post can be a solid cylinder or pyramid shape connected to an open drain area at the bottom whereby the fluid flows into the junction area. Valves present at each junction enable each individual blood component to be siphoned into an individual tube (for example, one for erythrocytes/red blood cells, one for the buffy coat (as applicable/needed), and one for plasma). In one embodiment, the valves are disposable to prevent any carry-over contamination. In another embodiment, the end of the collection tubes accept flexible tubing (to allow for apparatus motion) that are connected to the vacuum/pump via luer-lock fittings or similar.

Figure 7:
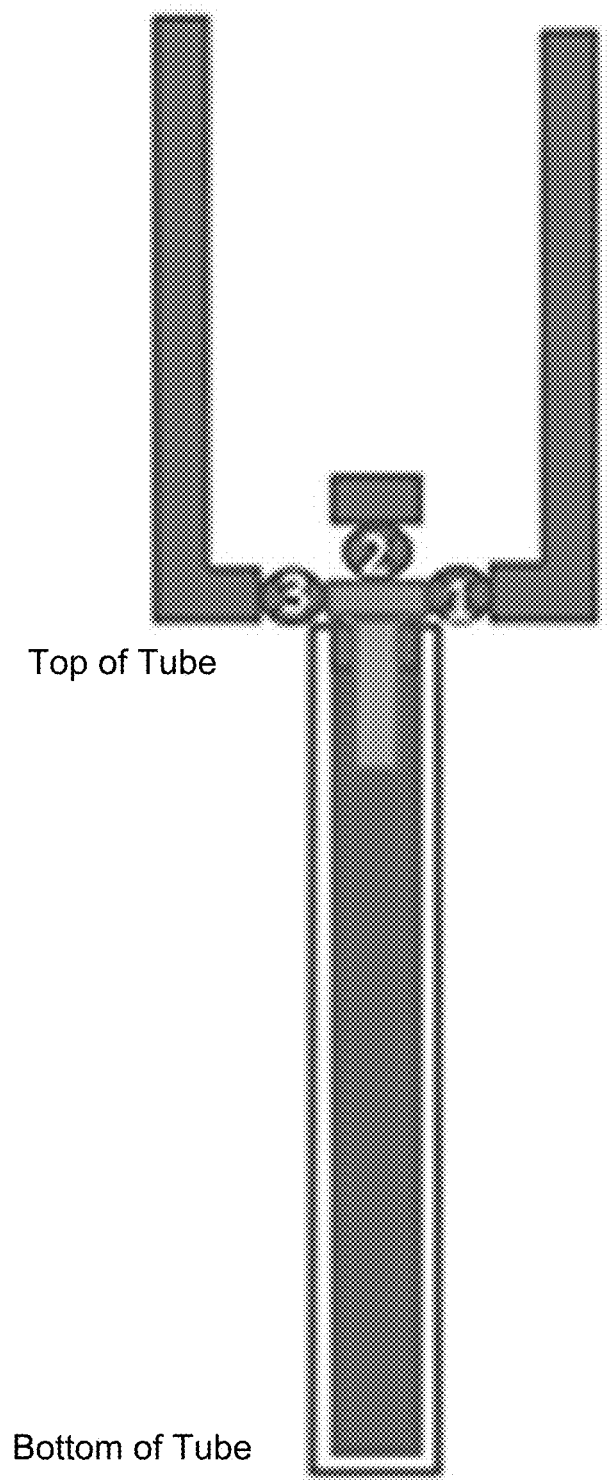
FIG. 7 is an exemplary diagram of a device for automatic fractionation of blood components.
Figure 8:
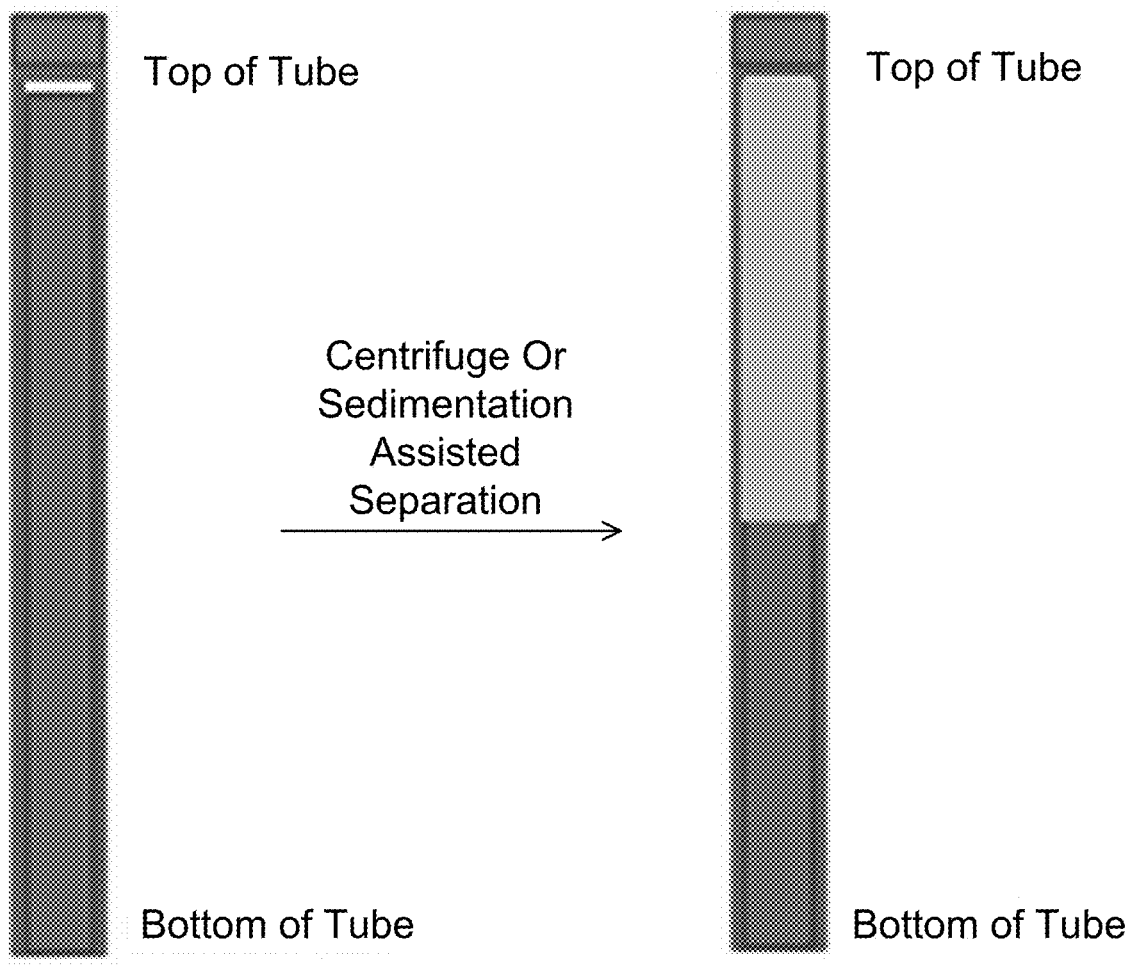
FIG. 8 is an exemplary diagram depicting alternate methods of separation in the device of FIG. 7.

Plasma naturally separates from other blood components if left to stand vertically for about an hour. As described herein, this process can be expedited through the addition of aggregation agents and/or application of aggregation means, for example, inclining the sample. It is therefore another embodiment of the present disclosure that commercially available blood collection tubes can be interfaced with the device depicted in FIG. 7, and whole blood accessed via the piercing post. In one embodiment, aggregation agents coupled with anti-coagulation agents could be introduced to the whole blood as part of the interface process (for instance through the piercing post) and then mixed through rotation of the system. In another embodiment, the device provides an incline to the sample container to help increase sedimentation rates. In an alternate embodiment, centrifugation can be used to separate blood component layers as shown in FIG. 8 as a secondary option to the user in the case that the initial sedimentation is insufficient.

In a further embodiment, the device is in communication with a controller and/or processor having non-transitory memory and capable of running software to control the function of the device and/or analyze the results obtained by the device. In another embodiment, one or more camera or visual input devices are additionally in communication with the controller and/or processor, such that the device can be visually monitored.

Once initial separation of the blood components has occurred, software and accompanying algorithms utilize input images to calculate how much vacuum is required to move the liquid column the appropriate distance and also to control the opening/closing of valves as required to direct fluid movement into the appropriate "branch". The algorithm locates, uses, and tracks the location of each component interface as active feedback control of the vacuum and valves. Appropriate venting is integrated into the design to ensure proper function.

In another embodiment, the use of active feedback control of any of the methods or devices provided herein may additional comprise an optical imaging system to monitor the sample sedimentation or separation of blood components. In one embodiment, the optical imaging system may contain, but does not require, a light source and one or more optics/filters. In another embodiment, the optical imaging system may contain one or more detectors. Detectors may include multiple-pixel array detectors (such as a CCD or CMOS image detector). In some embodiments, a commercial camera or video recorder may be the image detector. Detectors may be stationary or may be scanning.

The optical imaging system is under control of a main control and processing computer which directs the imaging system to monitor the sample sedimentation or separation of blood components. The main control and processing computer may also run software that uses as an input the data from the optical imaging system, including software using visual processing algorithms. The main control and processing computer may then also communicate instructions to mechanical means for operating the systems and devices provided herein, including for separating, moving and storing components of a sample.

FIGS. 9A-9F provide the device workflow. In FIG. 9A, a whole blood sample is present in the device. Following sedimentation shown in FIG. 9B, valve 1 is opened and the device is turned or tilted to ensure "clean" plasma is extracted through the valve system into one of the device arms, thereby mitigating the risk of potential contamination from other blood component layers. All valves are then closed (FIG. 9C), and the plasma remains in the device arm. In FIG. 9D, following plasma collection, the device rotates 180° to utilize gravity to bring other blood component fractions nearer to the valve system interface. Valves 2 and 3 can then be opened in turn to remove additional fractions into other device arms or associated vessels (FIGS. 9D-9E). In one embodiment, FIG. 9D is associated with collection of the buffy coat following plasma collection.

In some embodiments, the buffy coat layer may not separate sufficiently. In this case, the step shown in FIG. 9D can be omitted so that the system only separates plasma from the erythrocyte components. Instead of explicitly collecting the buffy coat layer, FIG. 9D can also be used to "waste" a portion of the total volume to remove any fraction of the plasma and erythrocyte layers that may have mixed at the interface. The workflow could be terminated at FIG. 9D or extended to FIGS. 9E and 9F if the user desires to capture the erythrocyte fraction in a separate tube. Each tube containing each fractioned layer can breakaway or is threaded for easy capping for the user's next step. In another embodiment, the plasma fraction could be delivered directly to a secondary container or the primary housing could be designed to detach from the unit (FIG. 9F).

It is an embodiment of the device described herein that both physical and mechanical approaches are utilized to achieve non-centrifugal blood component separation (for example, plasma from whole blood). In another embodiment, the automated fractionation of blood components is provided through computerized control via input from visual processing algorithms. In a further embodiment, the device can be integrated into existing analysis systems, eliminating the need for a separate, user controlled blood fractionation step.

The present disclosure includes an embodiment of a method of accelerating the separation of blood components from a sample, wherein the method comprises the steps of: providing a sample in a vessel; mixing the sample with one or more aggregating agents to form a mixture; and incubating the mixture. In a further embodiment, the method optionally includes the additional step of collecting one or more blood components from the separated sample. In another embodiment, the collected component is plasma. In a further embodiment, the collected plasma contains circulating cell-free DNA.

Another embodiment of the present disclosure provides for exposing the mixture of a sample and one or more aggregating agents to mechanical and/or physical aggregation means selected from (i) inclining the vessel; (ii) vibration; (iii) heating; (iv) tapping; and, (v) an electromagnetic field.

In a further embodiment, the aggregating agent comprises acute phase proteins or other macromolecules. In some embodiments, the aggregating agent is selected form the group consisting of Fibrinogen, Dextran, Hydroxyethyl Starch (HES), Polyvinylpyyrolidone (PVP), Polyethylene Glycol (PEG), and Gelatin. In further embodiments, the aggregating agent is fibrinogen. The fibrinogen can be present at a concentration of from 5 to 50 mg/ml, including at 30 mg/ml.

In one embodiment, the sample comprises whole blood.

In another embodiment, the method provided can include tapping the vessel and placing the vessel at an incline during incubation. In a further embodiment, the tapping of the vessel occurs for 10 minutes, and the incline is at 45°.

In yet another embodiment, there is provided an automated method to separate previously fractionated blood components, wherein the automated method utilizes the output from visual processing algorithms as active feedback control. Optical data from at least one fractionated blood sample can be captured by a photodetector, wherein the photodetector is in communication with a processor. The processor can utilize a visual processing algorithm to identify the location of or boundaries between individual blood components. The processor can be in communication with mechanical means to separate, move and store the components, and the location of, or the boundaries between, individual blood components can be utilized by the processor to control the mechanically-driven separation, movement, and storage of said components.

In one embodiment, any of the methods described herein can have the initial blood component fractionation is achieved by rapid sedimentation or centrifugation.

In some embodiments, the mechanical separation of the components occurs either during or after the sedimentation process. In further embodiments, the processor determines when the sedimentation process has finished.

In some embodiments, the processor is additionally in communication with a light source to illuminate the sample.

In further embodiments, the means to separate move and store the components comprises a device comprising a piercing post to receive a sample, wherein the sample vessel and the piercing post are in fluid communication, and at least a first and second arm, each extending perpendicular to length of the piercing post/sample vessel complex in opposite directions, wherein each at least first and second arm has a bend at the distal end of the perpendicular segment, and a second portion of each arm which extends from the bend in a direction perpendicular to the first segment and parallel to the piercing post, such that the distal ends of the piercing post and the second portion of the arms are in opposite directions. For example, the device used in such a method can be as provided in FIG. 7.

In another embodiment, valves separate the piercing post from each arm, and each valve is independently operable. In a further embodiment, the device can be freely rotated.

In one embodiment of the disclosure, there is provided a device for separating, moving and storing components of a biological sample, wherein the device comprises a piercing post to receive a sample, such that a sample vessel and the piercing post are in fluid communication, and at least a first and second arm extending perpendicular to the length of the piercing post/sample vessel complex in opposite directions, wherein each at least first and second arm has a bend at the distal end of the perpendicular segment, and a second portion of each arm which extends from the bend in a direction perpendicular to the first segment and parallel to the piercing post, such that the distal ends of the piercing post and the second portion of the arms are in opposite directions. For example, the device can be as provided in FIG. 7.

In another embodiment, valves separate the piercing post from each arm, and each valve is independently operable.

A further embodiment provides a method of separating blood components comprising using a controlled filter membrane that moves downward in a sample vessel at a rate equal to the anticipated sedimentation rate of the blood cells. In another embodiment, the rate of movement of the filter is controlled by active feedback control for the speed through input from optics/detection software.

A still further embodiment provides a method for separating plasma from other fractionated blood components. In one embodiment, an immiscible liquid is added to a sample vessel containing blood components. The immiscible liquid can be oil. The immiscible liquid can be added to the sample vessel before, during or after the fractionation of the blood components. In one embodiment, the vessel containing the immiscible liquid and the blood components is tilted to a pinching position, where the immiscible fluid pinches off a portion of the plasma from the remainder of the blood components. In a further embodiment, the sample vessel is then tilted back to the starting position, where at least a portion of the plasma is now isolated within the immiscible fluid.

In a further embodiment, there is provided markings on the sample vessel to indicate to the user the amount of tilting that is necessary to achieve the pinching position.

In another embodiment, there is an automated means for tilting one or more sample vessels to achieve an isolated portion of plasma. In a further embodiment, optical feedback can be used as part of the automation process.

EXAMPLES

Example 1: Sedimentation with Aggregation Agent

An experimental protocol was developed to identify and test which blood aggregation agent most effectively increased sedimentation rate while producing the greatest plasma yield and purity. Blood aggregation agents were selected based on potential for blood cell aggregation and experimental feasibility as follows:

TABLE 1

Blood Aggregation Agents tested.

| Agent | Average Molecular Weight (g/mol) | Concentration of Agent Tested (mg/mL whole blood) |
|---|---|---|
| Fibrinogen | N/A | 4, 6, 8, 10, 15, 20, 25 |
| Dextran | 70,000 | 10, 25, 30, 40, 50, 60, 70 |
| Hydroxyethyl Starch (HES) | N/A | 10, 30, 50, 75, 100 |
| Polyvinyl-pyyrolidone (PVP) | 360,000 | 2.5, 10, 25, 50, 100 |
| Polyethylene Glyocl (PEG) | 20,000 | 10, 20, 30, 50, 75 |
| Gelatin (bovine) | N/A | 0.5, 1, 5, 15, 30, 50, 100 |

Solubility of each aggregation agent was tested in 250 μL of each of a 3.8% Sodium Citrate stock and deionized (DI) water. Results are provided in Table 2.

TABLE 2

Solubility Experiment Results.

| Agent | 3.8% Sodium Citrate | DI Water |
|---|---|---|
| Fibrinogen | soluble | Soluble |
| Dextran | soluble | Soluble |
| Hydroxyethyl Starch (HES) | insoluble | Insoluble |
| Polyvinylpyyrolidone (PVP) | insoluble | Insoluble |
| Polyethylene Glyocl (PEG) | soluble | Soluble |
| Gelatin (bovine) | insoluble | Insoluble |

Sedimentation testing was performed using Erythrocyte Sedimentation Rate (ESR) kits, as are commonly used in a clinical setting. ESR kits measured the amount of plasma separated from whole blood. ESR kits contained a disposable pipette and a vial pre-filled with 250 μL 3.8% Trisodium Citrate anticoagulant. 1 mL of whole human blood containing K2 EDTA anticoagulant was added to an ESR vial containing either (i) the 250 μL 3.8% Trisodium Citrate anticoagulant or (ii) 250 μL of a water matrix. An aggregate agent from Table 1 was also added to the ESR vial. Each of the aggregate agents shown in Table 1 were tested in both 250 μL 3.8% Trisodium Citrate anticoagulant and 250 μL of a water matrix at each concentration amount. This allowed for a comparison of the differences in sedimentation when the additional Trisodium Citrate anticoagulant was present and absent. Once the ESR vials were fully prepared, they were placed on a stand at a 45° angle.

Figure 10:
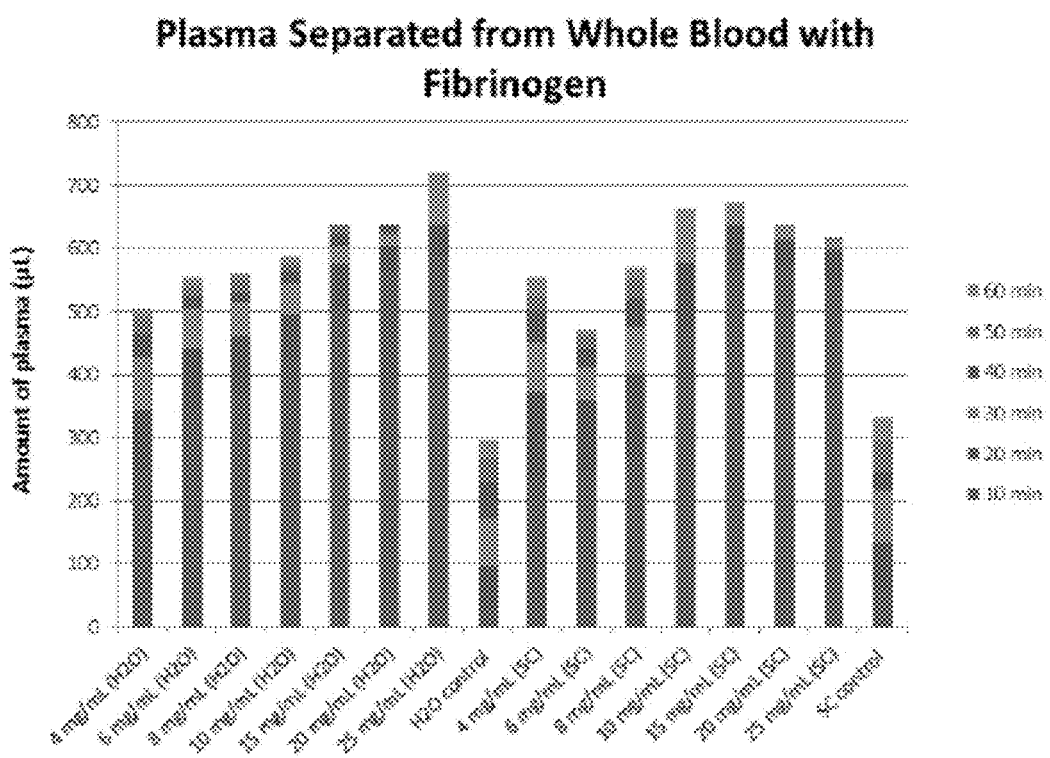
FIG. 10 is a graph showing plasma separation over time from whole blood using fibrinogen as an aggregation agent.

Samples were evaluated every 10 minutes to determine the amount of plasma separated from the whole blood samples. Use of fibrinogen as an aggregate agent resulted in the greatest plasma yield, with the most efficient concentrations of Fibrinogen being 25 mg/mL in water and 15 mg/mL in Trisodium Citrate. In both instance, the period of highest plasma yield occurred from 0-10 minute incubation. Results from the Fibrinogen experiments are shown in FIG. 10.

The least successful aggregation agent was HES, likely due to the HES coming out of solution during sedimentation.

Results for selected samples from all aggregation agents are shown in Table 3. Table 3 shows that other aggregation agents that performed well included PEG 35 mg/mL in Trisodium Citrate and Dextran 25 mg/mL in Trisodium Citrate.

TABLE 3

Aggregation agent results.

| Aggregate | Matrix | 10 min. | 20 min. | 30 min. | 40 min. | 50 min. | 60 min. |
|---|---|---|---|---|---|---|---|
| Fibrinogen | SC + 15 mg/mL | 564.2 | 637.8 | 662.3 | 662.3 | 662.3 | 672.2 |
|  | W + 25 mg/mL | 588.8 | 637.8 | 721.2 | 721.2 | 721.2 | 721.2 |
| Dextran | SC + 25 mg/mL | 466.1 | 539.7 | 564.2 | 593.7 | 603.5 | 613.3 |
|  | W + 10 mg/mL | 137.4 | 343.4 | 426.8 | 471 | 500.4 | 510.3 |
| HES | SC + 20 mg/mL | 93.2 | 196.3 | 279.7 | 338.5 | 372.9 | 417 |
|  | W + 10 mg/mL | 49.1 | 166.8 | 235.5 | 314 | 353.3 | 377.8 |
| PVP | SC + 25 mg/mL | 34.3 | 294.4 | 407.2 | 456.3 | 485.7 | 505.3 |
|  | W + 25 mg/mL | 0 | 54 | 215.9 | 343.4 | 397.4 | 431.8 |
| PEG | SC + 35 mg/mL | 9.8 | 564.2 | 613.2 | 637.8 | 637.8 | 637.8 |
|  | W + 35 mg/mL | 0 | 73.6 | 260 | 328.7 | 372.9 | 421.9 |
| Gelatin | SC + 10 mg/mL | 63.7 | 220.7 | 309.1 | 377.7 | 431.8 | 466.1 |
|  | W + 10 mg/mL | 9.8 | 98.1 | 245.3 | 318.9 | 368 | 392.5 |

SC = Trisodium Citrate.
W = water.

A second round of testing was performed using a 30 minute sedimentation run (measurements taken at 2, 4, 6, 8, 10, 15, 20, 25 and 30 minutes) for 4 different aggregation agent/matrix combinations: Fibrinogen 25 mg/mL in water, Fibrinogen 15 mg/mL in Trisodium Citrate, PEG 35 mg/mL in Trisodium Citrate and Dextran 25 mg/mL in Trisodium Citrate. Each sample was run in triplicate, with whole blood in the presence of Trisodium Citrate or water as controls. To reduce variability, whole blood for the triplicate samples was pulled from the same vacutainer.

Figure 11:
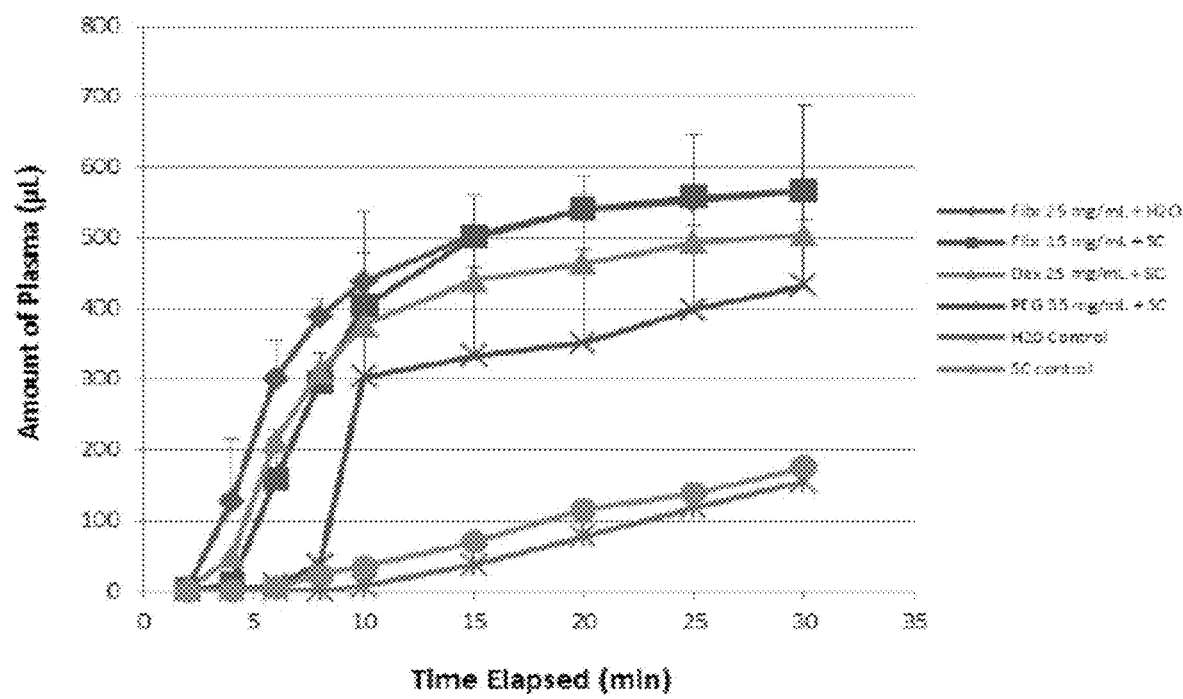
FIG. 11 is a graph showing average whole blood sedimentation over a 30 minute period with various aggregation agents.

Results are shown in FIG. 11. The fibrinogen again yielded the highest amount of plasma. The fibrinogen in water sample began sedimentation earlier than the fibrinogen in trisodium citrate. The addition of fibrinogen yielded approximately 3× more plasma in comparison to the control samples within 30 minutes. The PEG samples yielded the least amount of plasma and were slower to begin sedimentation. High deviation in the PEG results were due to a clog in the ESR kit.

Example 2: PCR Inhibition by Aggregation Agent

The level of PCR inhibition caused by the presence of different blood aggregation agents and blood anticoagulant agents was determined. Aggregation agents were spiked into whole blood which was then analyzed. Samples were tested in both trisodium citrate and water: Fibrinogen (25 mg/mL) in water, Fibrinogen (15 mg/mL) in trisodium citrate, PEG (35 mg/mL) in trisodium citrate and Dextran (25 mg/mL) in trisodium citrate. Whole blood, whole blood with water and whole blood with tri sodium citrate, with and without DNA were used as controls.

DNA was purified from the samples using a PureLink genomic DNA purification kit, with the resulting DNA quantified using NanoDrop. All DNA was diluted to 50 ng/μL to normalize the samples. Normalized samples then underwent qPCR using a protocol for UCE17 (U.S. Pat. No. 9,554,422, U.S. Published Patent Application 20170325288, and other related family members). Quantitation cycle (Cq) values and the results of a thermal melt analysis are shown in FIGS. 12A-12C.

Example 3: Plasma Purity

Whole blood was spiked into a water or trisodium citrate matrix with the dissolved aggregating agent to be tested. Agents tested included Fibrinogen (25 mg/mL) in water, Fibrinogen (15 mg/mL) in trisodium citrate, PEG (35 mg/mL) in trisodium citrate, and Dextran (25 mg/mL) in trisodium citrate. Controls included whole blood, trisodium citrate and water controls, as well as a plasma control (BioreclamationIVT). Samples were placed into Eppendorf tubes for 30 minutes at a 45° angle to allow sedimentation to occur. Also tested were centrifugation at 2000 RCF and 100 RCF, as well as sedimentation at 90°. Following sedimentation, plasma was extracted for analysis.

Figure 13:
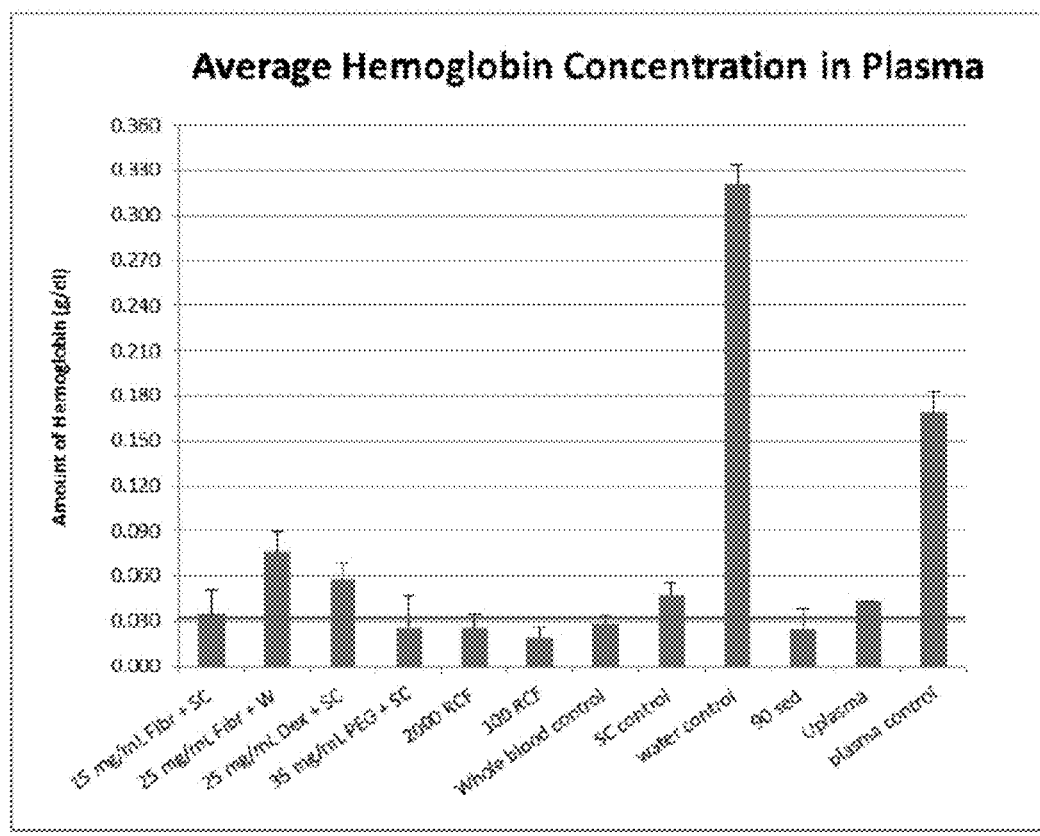
FIG. 13 is a graph showing hemoglobin assay results as an indicator of plasma purity.

A hemoglobin assay (Cayman Chemical) was run on the extracted plasma. As hemoglobin is found in red blood cells, a lower hemoglobin concentration was indicative of a more purified plasma sample. Plasma was diluted 1:1 with nuclease free water to lyse red blood cells prior to determining the hemoglobin concentration in the plasma sample. PEF had the lowest concentration of hemoglobin, followed by fibrinogen in trisodium citrate, as shown in FIG. 13.

Figure 14:
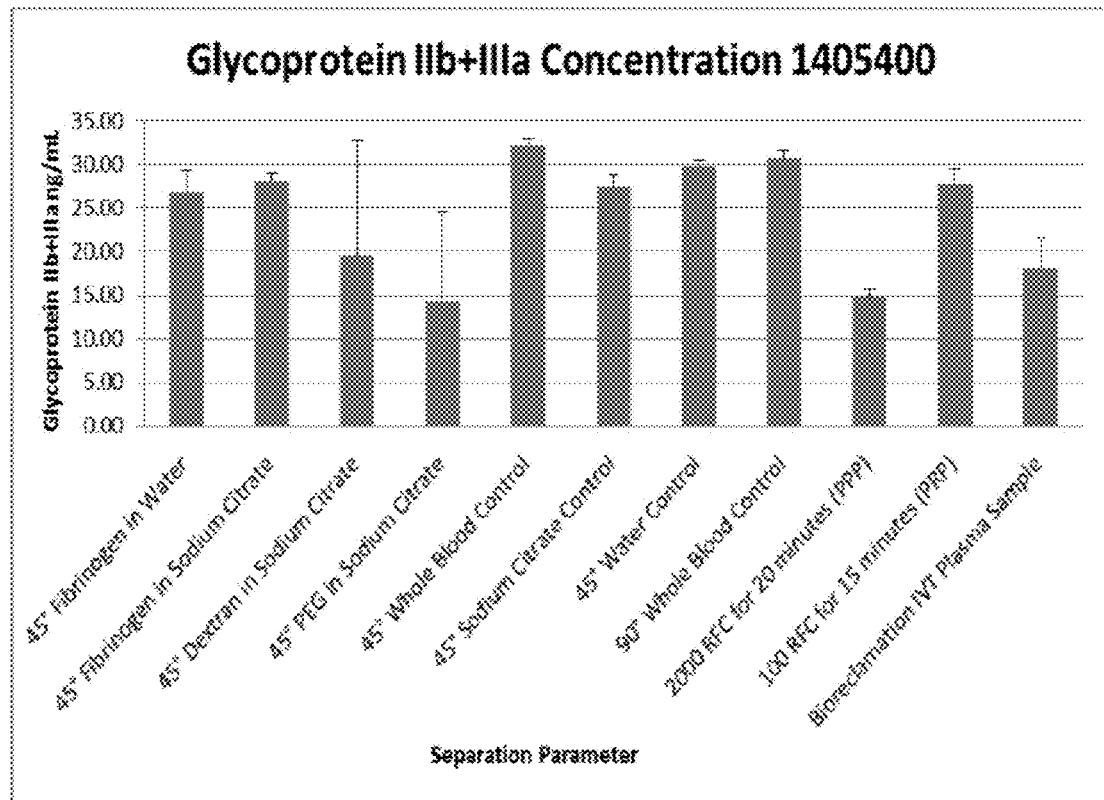
FIG. 14 is a graph showing glycoprotein IIb+IIIa assay results as an indicator of plasma purity.

A platelet glycoprotein IIb/IIIa ELISA (abcam) was also performed on the plasma samples. Glycoprotein IIb/IIIa is a receptor for fibrinogen and other blood cell coagulation factors, which is primarily found on platelets. Therefore, a lower concentration of glycoprotein IIb/IIIa was indicative of a more purified plasma sample. As shown in FIG. 14, the sample containing PEG that was positioned at 45° during sedimentation had the lowest glycoprotein concentration. In general, samples where sedimentation was performed at 45° had a lower glycoprotein concentration than those samples where sedimentation occurred at 90°.

Example 4: Blood Aggregation Agents

Blood aggregation agents were narrowed to the three most commonly used in literature: Dextran of molecular weight (MW) 70K and 150K from *Leuconostoc mesenteroides* and Fibrinogen (FN) from human plasma.

In this study, a Westergren erythrocyte sedimentation rate (ESR) kit (Globe Scientific, USA) was used to study blood sedimentation rate. The kit consisted of a vial pre-filled with 4% sodium citrate, 180 mm long Westergren tube, and a tube stand (see FIG. 5). One ml of healthy donor blood with k2EDTA anticoagulant (BioreclamationIVT, USA) was used per test. The three different aggregation agents at three different concentrations were tested at 90° tube-to-surface angle. Dextran of molecular weight (MW) 70K and 150K from *Leuconostoc mesenteroides* (Sigma-Aldrich, USA) were used at concentrations of 10, 60, and 100 mg/ml. Fibrinogen (FN) from human plasma (Sigma-Aldrich, USA) was used at concentrations of 5, 10, and 15 mg/ml. A fourth group of samples were tested using the three aggregation agents at 45° tube-to-surface angle.

Figure 15:
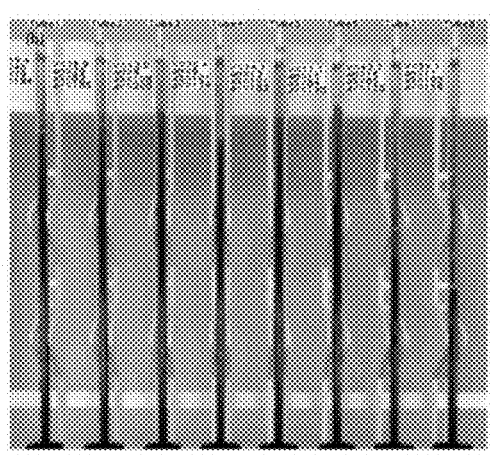
FIG. 15 is a diagram showing the set up of samples for monitoring by an imaging device.

Aggregation agents were added first to the ESR vial and mixed with the anticoagulant using a vortex for 5 minutes. Following that, blood was added and mixed with the anticoagulant and aggregation agents by gently inverting up and down 10 times. Blood was then pushed into the Westergren tube and left standing for 60 min to allow sedimentation to occur. All test runs were video recorded, and plasma yield over time was detected and measured using software "Plasma Separation" (internally developed) (FIG. 15). FIG. 15 provides a snap shot of the software "Plasma Separation" used to detect plasma yield by tracking color change in the tubes. The area of the tube identified by the software is clearly outlined at the top of each tube.

Figure 16:
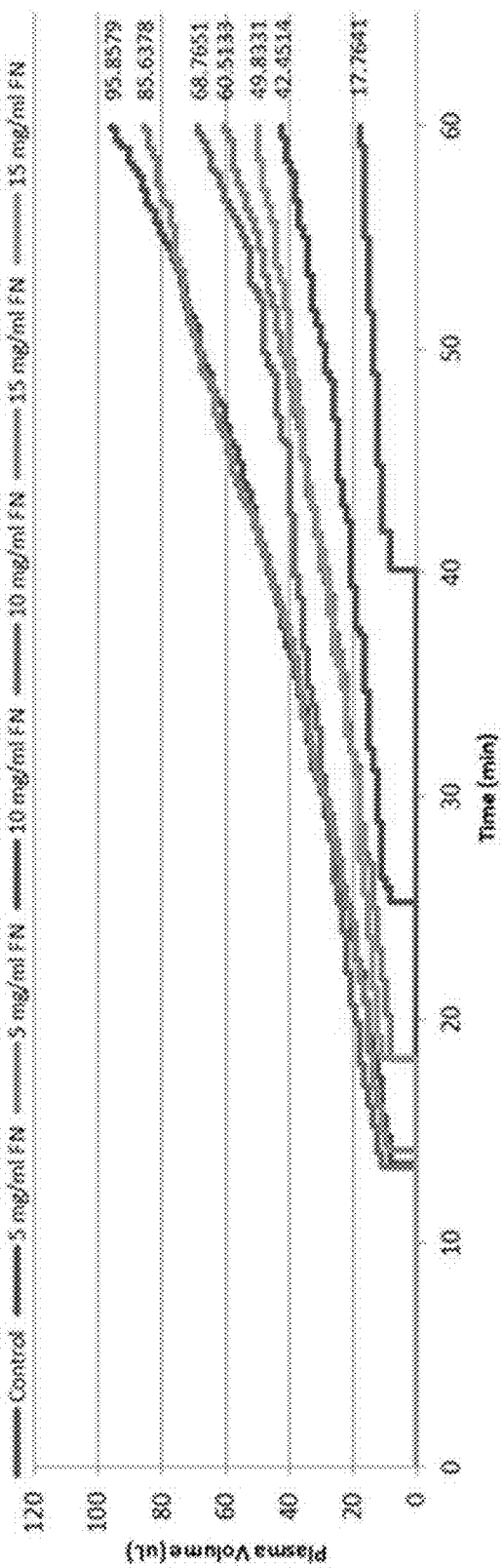
FIG. 16 is a chart showing plasma volume vs. time.
Figure 17:
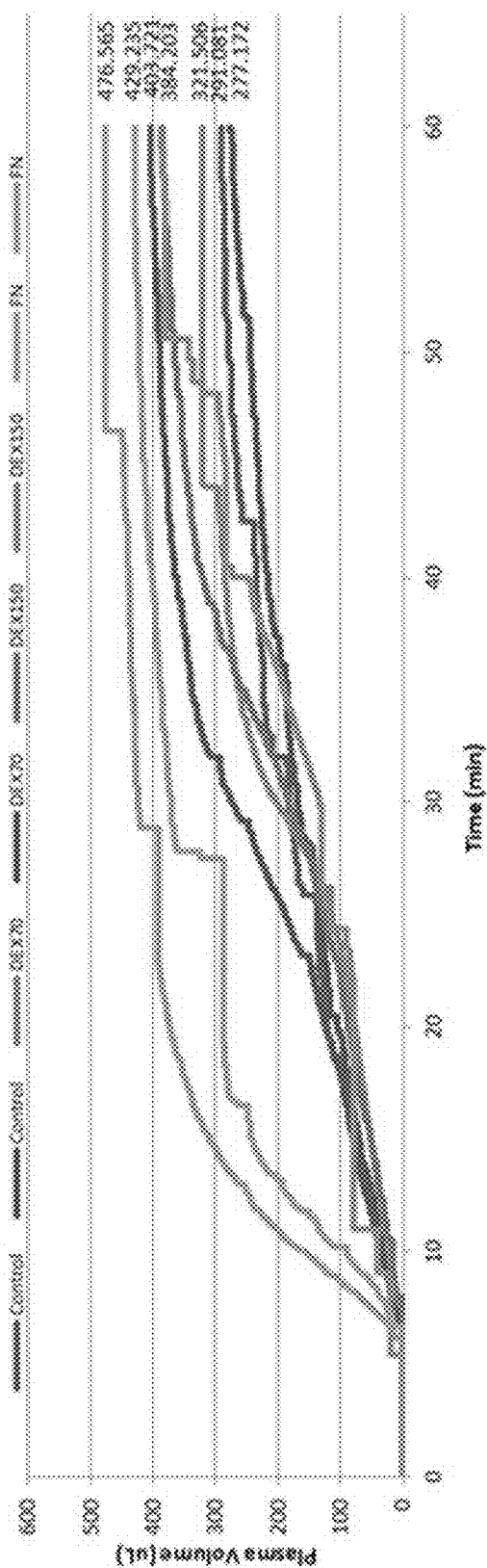
FIG. 17 is a chart showing plasma volume vs. time.

Each aggregation agent, Dextran MW70, Dextran MW150, and Fibrinogen, were tested at three different concentrations with a tube-to-surface angle of 90°. Fibrinogen at its highest selected concentration of 15 mg/ml produced the highest sedimentation rate. Higher concentrations up to 30 mg/ml were tested in subsequent experiments (see section 2.3.4.2). After 60 minutes the plasma yield for the 15 mg/ml FN was at ~100 uL (see FIG. 16). At 45° tube-to-surface angle, all the three different aggregation agents were tested again. A significant increase in the plasma yield was observed and recorded in all three aggregation agents, with the 15 mg/ml FN producing the highest yield. After 60 minutes the plasma yield for the 15 mg/ml FN was ~450 uL, which was 4 times higher yield than that recorded at a tube-to-surface angle of 90° (see FIG. 17). Based on these results, aggregation agents were down selected to Fibrinogen with concentration of 15 mg/ml.

Fibrinogen at 15 mg/mL had the best aggregation effect on blood cells, and thus the highest sedimentation rate compared to Dextran. Combining aggregation agents with the tube at a 45° inclined angle when compared with 90° accelerated the sedimentation process by more than 4 fold.

Example 5: Rapid Sedimentation

Experiments were performed to investigate additional methods to accelerate blood sedimentation rate, including aggregation agent concentration, incline angle, tapping and vibration, dilution and tube geometry.

The same experimental setup was used as in Experiment 4: Blood Aggregation Agents, to independently test five different parameters to ascertain their impact on sedimentation rates. First, some aggregation agents were tested at higher concentrations, up to 2 fold higher than in previous experiments. In a second set of experiments, sedimentation was tested at two different tube angles, 45° and 25°. The third set of experiments tested the effect of mechanical forces such as tapping and vibration on blood sedimentation rate. A 15000 RPM 3 VDC vibrator motor was used to induce some mechanical force to assist blood cells in sedimentation. The vibrator was powered by 3V batteries and fixed directly on the middle of the ESR tube rack. A fourth set of experiments tested the effect of diluted blood samples on sedimentation rate. 1×PBS (Sigma-Aldrich, USA) was used to dilute blood samples at concentrations of 1:1, 1:2, and 1:4. Blood samples were brought to room temperature before PBS buffer was added at the desired concentrations. Samples were mixed by gently inverting the tube up and down 10 times. In the last set of experiments, a 5 mm diameter pipette was used (Sigma-Aldrich, USA) to replace of the 2.5 mm ESR tube to test sedimentation in larger diameter tubes.

The three aggregation agents used in Example 4 were tested again but at higher concentrations. Dextran with molecular weights, 70K and 150K, did not show any significant increase in plasma yield even at twice the concentration used in previous experiment. This result was somewhat expected as the literature shows that dextran's aggregation to concentration relation follows a bell like shape, and thus increasing the concentration will not always increase the aggregation effect. In contrast, the aggregation to concentration effect in the case of Fibrinogen seemed to be linear and directly proportional. However, when Fibrinogen was used at twice the concentration used in the previous experiment (increasing from 15 mg/ml to 30 mg/ml), the plasma yield and sedimentation rate were significantly lower (see Table 4). This could be due to increase in blood viscosity at higher Fibrinogen concentrations, which slows down the plasma separation process. Based on this result, Fibrinogen at 15 mg/ml concentration was found to have the best plasma yield, and was selected for subsequent experiments.

TABLE 4

Plasma yield, in terms of column height, over time with aggregation agents, 45° angle.

|  | 10 min | 20 in | 30 min |
|---|---|---|---|
| Control | 7 mm | 20 mm | 25 mm |
| Control | 10 mm | 25 mm | 40 mm |
| DEX70 | 18 mm | 64 mm | 95 mm |
| DEX70 | 18 mm | 45 mm | 70 mm |
| DEX150 | 0 mm | 35 mm | 60 mm |
| DEX150 | 0 mm | 10 mm | 20 mm |
| FN15 | 100 mm | 110 mm | 120 mm |
| FN15 | 90 mm | 100 mm | 110 mm |
| FN30 | 55 mm | 65 mm | 75 mm |
| FN30 | 40 mm | 55 mm | 70 mm |

Highest plasma yield is shown in the two rows marked FN15.

Figure 18A:
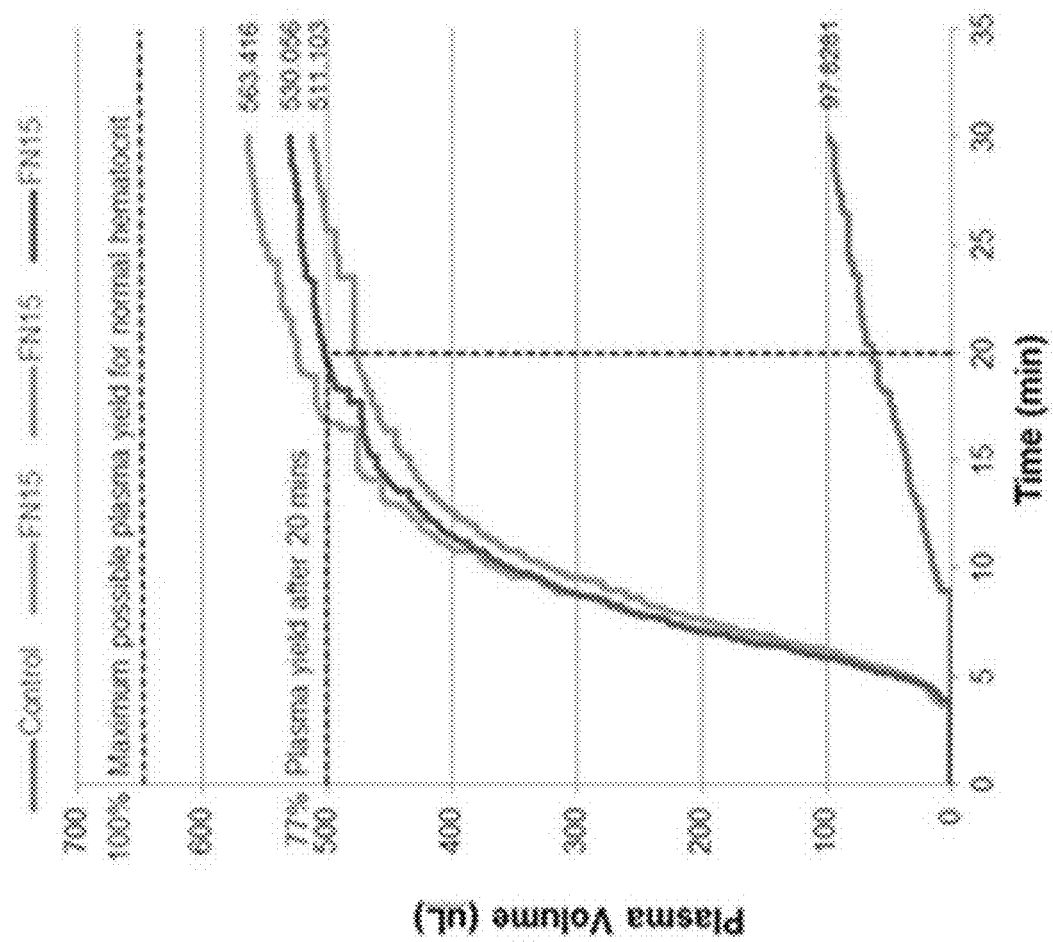
FIG. 18A is a chart showing plasma volume vs. time.
Figure 18C:
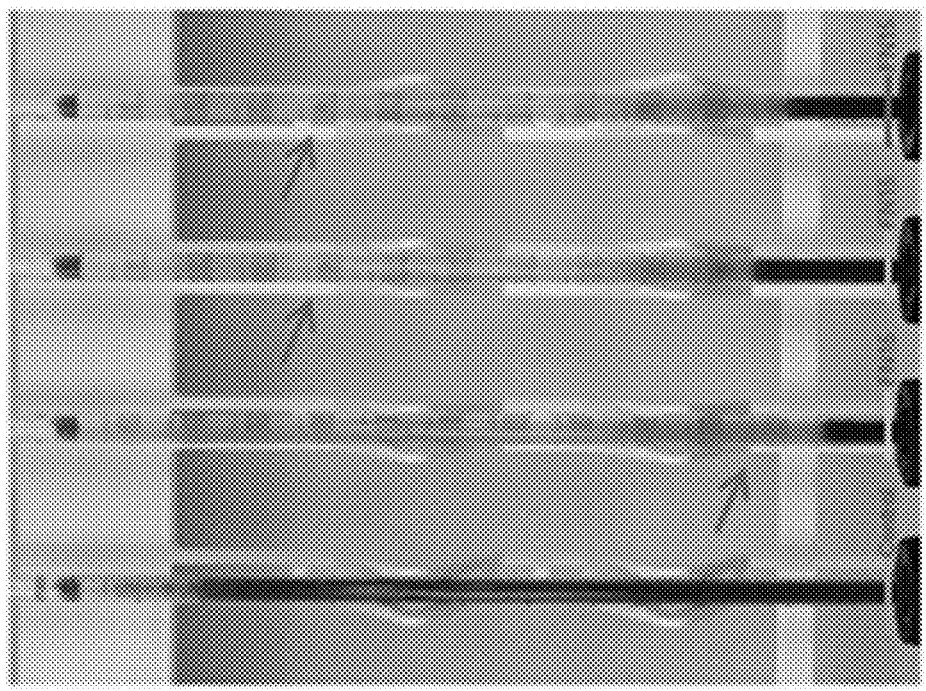
FIGS. 18B and 18C are photographs showing samples before and after tapping.
Figure 18B:
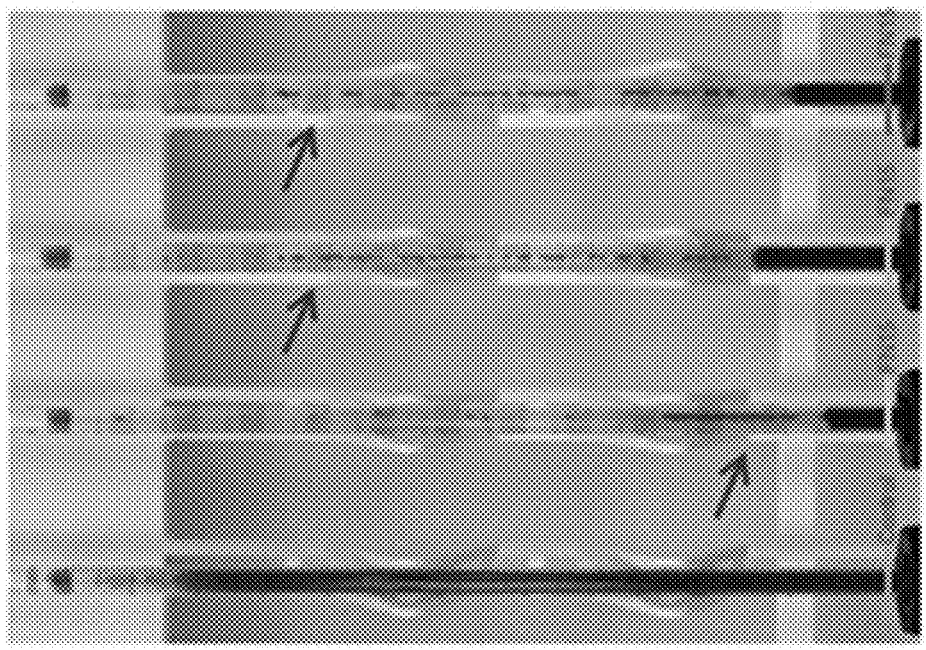

The highest plasma yield and separation efficiency was achieved with a combination of parameters including Fibrinogen as aggregation agent, a 45° incline angle, and 10 minutes tapping after sedimentation. At 20 minutes ~500 uL of plasma was separated with a yield of ~77% from total plasma in the sample, and 92% at 30 minutes (see Table 5). Tapping the tubes after sedimentation helped in eliminating cells settled on the side of the tube and thus enhanced the plasma purity (see FIGS. 18A-18C).

TABLE 5

Plasma yield over time with aggregation agents - 45° angle - Tapping.

|  | 10 min | 20 min | 30 min |
|---|---|---|---|
| Control | 0 mm | 10 mm | 15 mm |
| FN15 | 75 mm | 105 mm | 115 mm |
| FN15 | 65 mm | 95 mm | 105 mm |
| FN15 | 75 mm | 105 mm | 105 mm |

The highest plasma yield achieved over time was within the first 20 minutes. Between 20 to 30 minutes the plasma yield increased but not significantly, and due to time requirements, it was found that the 20 minutes provides the best yield to time output (highlighted in green).

FIG. 9A shows that the highest plasma yield output used the combination of Fibrinogen, 45° angle, and tapping. FIGS. 9B-9C depict RBC aggregates before and after tapping. The test was also done with Fibrinogen at a 45° angle.

Using a mechanical vibrator as an alternative for the tapping process was also tested. Although the plasma purity was enhanced by pushing the cells away from the tube walls using the mechanical vibrator, the final plasma yield was less at 20 minutes compared to the tapping method. Even at 30 minutes the yield was not significantly improved. This could be due to turbulent flow induced by the vibration force that might have a slow blood sedimentation rate (see Table 6).

TABLE 6

Plasma yield over time with aggregation agents - 45° angle- Vibration.

|  | 10 min | 20 min | 30 min |
|---|---|---|---|
| Control | 5 mm | 15 mm | 25 mm |
| FN15 | 25 mm | 70 mm | 85 mm |
| FN15 | 40 mm | 95 mm | 105 mm |
| FN15 | 20 mm | 65 mm | 80 mm |

Low yield relative to tapping method is highlighted in shown in the column 20 min.

Samples were also tested at a 25° incline angle. Although reaching a similar plasma yield at 30 minutes, the separation efficiency was much lower compared to the 45° incline angle. At a 90° angle (tube is perpendicular to the surface); blood cells are in complete free fall while experiencing the least amount of friction with the tube wall. As the angle decreases (the tube is tilted towards the surface), blood cells start to slide on the tube wall instead of being in complete free fall. This can cause blood cells to stick to the wall thus slowing the sedimentation process (see Table 7).

TABLE 7

Plasma yield over time with aggregation agents - 25° angle.

|  | 10 min | 20 min | 30 min |
|---|---|---|---|
| Control | 5 mm | 15 mm | 30 mm |
| FN15 | 10 mm | 30 mm | 80 mm |

TABLE 7-continued

Plasma yield over time with aggregation agents - 25° angle.

| | 10 min | 20 min | 30 min |
|---|---|---|---|
| FN15 | 20 mm | 40 mm | 110 mm |
| FN15 | 25 mm | 35 mm | 100 mm |

Low separation efficiency due to settled cells is highlighted in red.

Samples were also tested in 5 mm diameter glass tubes. The wider diameter tubes achieved plasma yields similar to the 2.5 mm tubes. In this test, plasma yield was measured in terms of volume, and converted to height to facilitate comparisons with other data sets. At 20 minutes ~400 uL of plasma was separated with a yield of 61% (See Table 8).

TABLE 8

Plasma yield over time with aggregation agents - 45° angle - 5 mm diameter tube.

| | 10 min | 20 min | 30 min |
|---|---|---|---|
| Control | 0 mm | 0 mm | 0 mm |
| FN15 | 67 mm | 95 mm | 97 mm |
| FN15 | 44 mm | 81 mm | 85 mm |
| FN15 | 71 mm | 104 mm | 108 mm |

Best plasma yield and purity at shortest time is in the 20 minute column.

Results of the experiments showed that a combination of fibrinogen as an aggregation agent, 45° incline, and tapping after sedimentation gave the best output for plasma yield and purity. Further, using mechanical vibration and tapping provided similar results.

Example 6: Dead-End Filtration and Sedimentation

Figure 19:
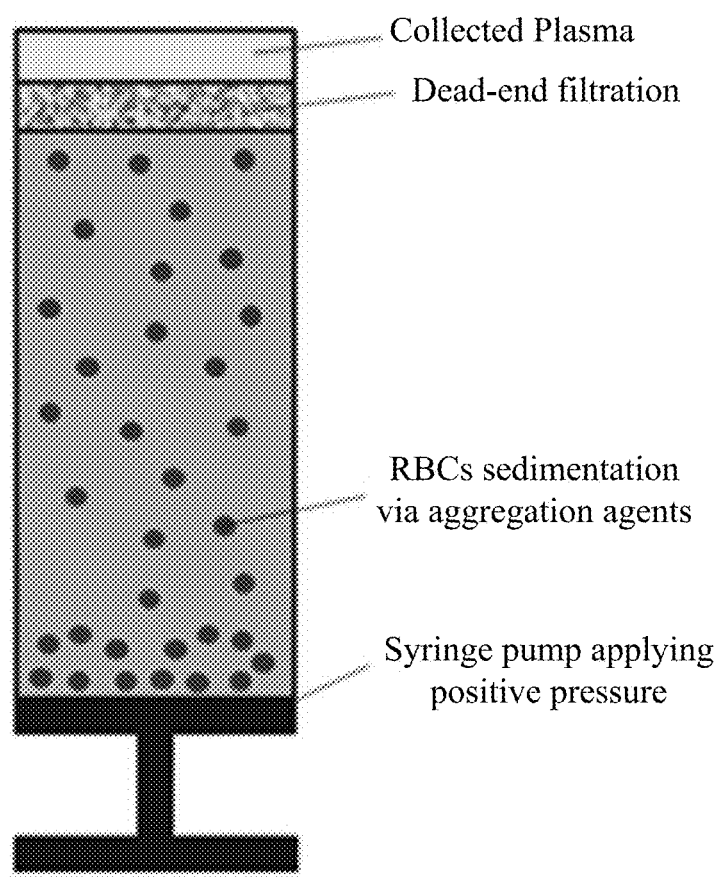
FIG. 19 is a schematic of a dead end filter apparatus.

Aggregation agents were used to induce aggregation of blood cells and accelerate the sedimentation process. Once plasma was partially separated from blood cells, it was pushed through a membrane to filter out any remaining blood cells in the plasma. FIG. 19 is a schematic depicting the embodiments tested in this example. The ideal experimental results included high plasma yield (separated plasma volume ~1 ml), high plasma efficiency (plasma purity), separation time of approximately 15 minutes, 30-65% whole blood hematocrit with no dilution and the ability to process approximately 2 ml blood sample volume.

In this example, six filtration membranes were selected. Each one represented a category of membrane with different characteristics or features such as pore size, material or structure. Three of the selected membranes had a symmetric structure, where the membrane pore size is constant and uniformly distributed. The other three membranes had an asymmetric structure, where membrane pores range in size and distribution (see Table 9). The membranes were tested using a blood mimicking fluid (BMF). The BMF was composed of 55% replicator fluid (Vascular Simulations, USA), 45% 3-10 um glass microbeads (Corpuscular, USA), and 1% 10-25 um glass microbeads (Corpuscular, USA). The replicator fluid mimics plasma's physical and mechanical characteristics, while the microbeads mimic red and white blood cell geometric composition.

TABLE 9

List of selected filtration membranes

| Filter | Manufacturer | Feature |
|---|---|---|
| Vivid GR | Pall | Asymmetric Polysulfone |
| Type A/D Glass Fiber | Pall | Asymmetric Glass Fiber 3 um |
| VF2 | GE Life Sciences | Asymmetric Glass Fiber |
| Nuclepore 3 um | GE - Whatman | Symmetric Polycarbonate 3 um |
| Nuclepore 5 um | GE - Whatman | Symmetric Polycarbonate 5 um |
| Cyclopore 5 μm | GE - Whatman | Symmetric Polycarbonate 5 um |

A previously built pressure station was used to test the filtration membranes. The test rig consisted of a peristaltic pump that provided positive and negative pressure. The pressure was maintained constant using a pressure sensor that provided feedback to the pump to regulate the pressure and was controlled by Pressure Station software. Thirteen and 25 mm diameter stainless steel filter holders (EMD Millipore, USA) were used to house the filter membranes (see FIGS. 20A-20D). Samples were tested under constant −5 PSI for 5 minutes.

Figures 20A, 20B, 20C:
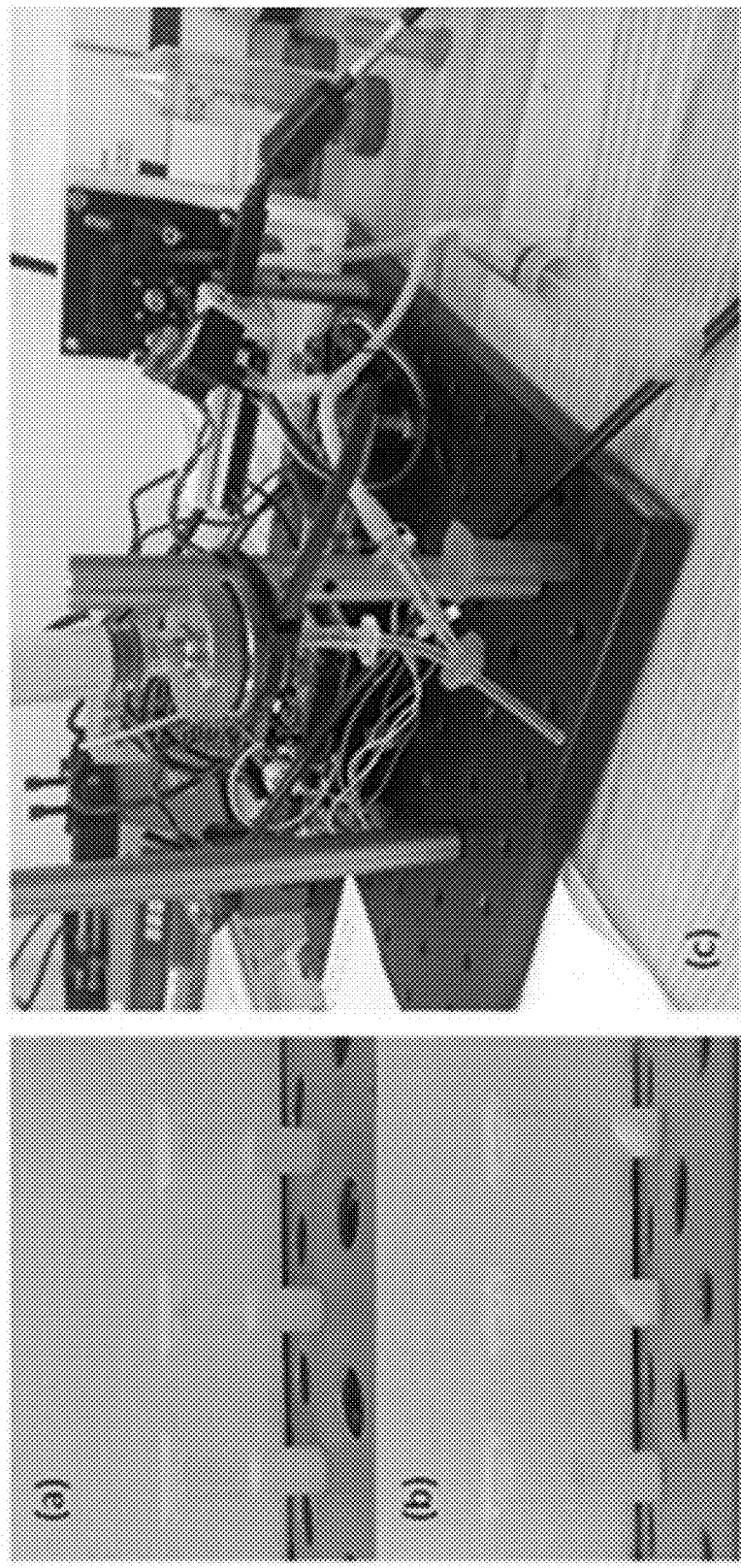
FIGS. 20A-20D are photographs and diagrams of a test set up.
Figure 20D:
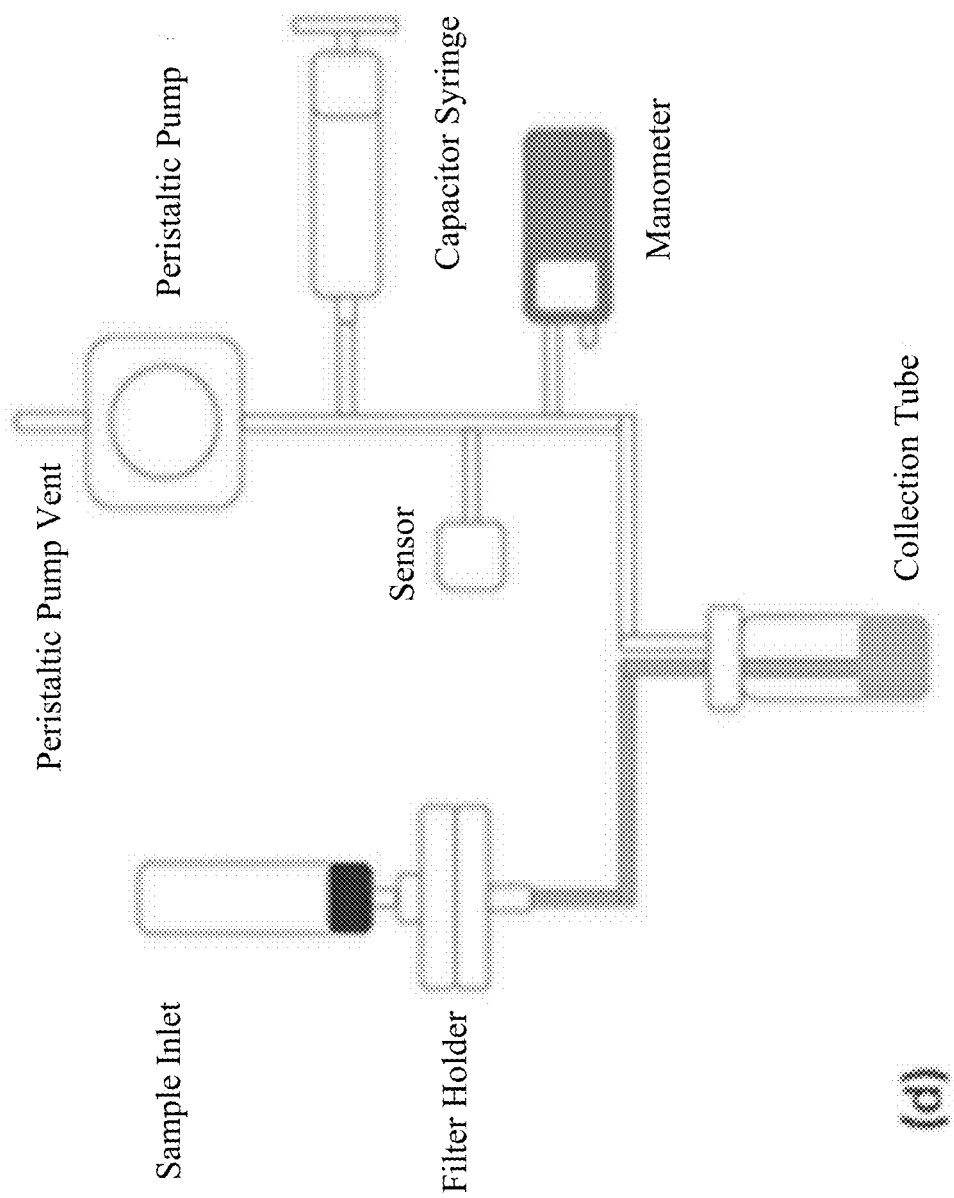

FIG. 20A shows a 1 ml test sample comprising 0.5 ml 3-10 um glass microbeads in 0.5 ml replicator fluid. The sample is shown in FIG. 20B following centrifugation. FIG. 20C is a picture of the test rig. Pressure was measured at different points on the test rig as a control. Maximum pressure from the peristaltic pump was −5 PSI. It dropped down to −4.7 PSI at the vent chamber. At the filter holder it dropped down to −3.5 PSI which is the maximum pressure applied on the filter membrane using this set up. A schematic drawing for the test setup is provided in FIG. 20D.

Results were recorded in FIG. 21-24. Red colored cells represent failed tests. Failures due to clogging are notated with (c), and failures due to filter breakdown are notated (F). Green colored cells represent a successful test. Grey cells represent tests that were not completed due to predicted results based on previous testing outcomes. Tests held under manual pressures above −5 PSI are notated with (↑).

From testing the 6 filters with 50% 3-10 um microbeads (mimicking RBCs) more clogging was noted when compared to the 1% 10-25 um microbeads (mimicking WBCs), which suggests that one important source of the clogging in blood is the density of RBCs and not the size of the WBCs. Also, asymmetric membranes (Vivid GR, Type A/D Glass Fiber, and VF2) showed better performance compared to symmetric membranes (Nuclepore 3 μm, Nuclepore 5 μm, and Cyclopore 5 μm). The Vivid membrane had the highest filtration but only worked under high pressures. On the other hand, the two glass fiber membranes (Type A/D and VF2) showed similar results.

Figure 21:
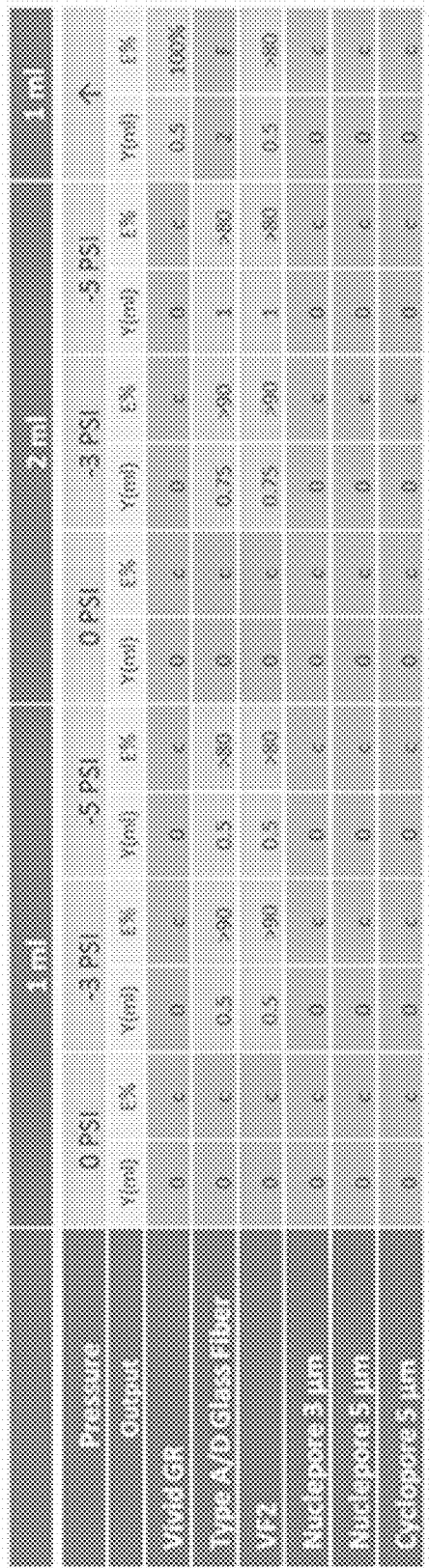
FIG. 21 is a table showing filtration test results.
Figure 22:
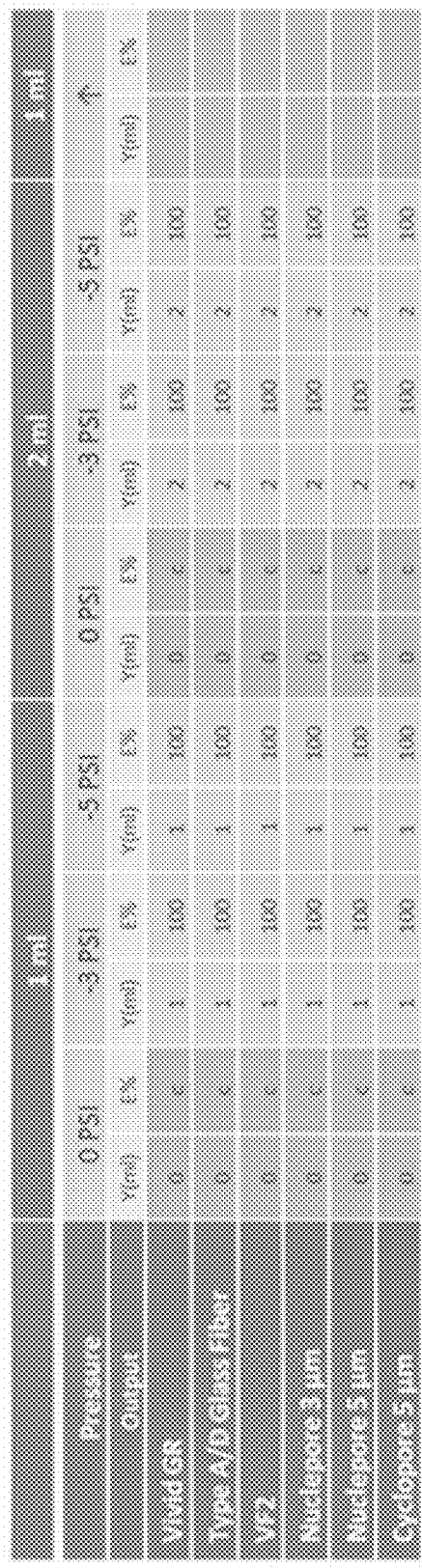
FIG. 22 is a table showing filtration test results.
Figures 23, 24:
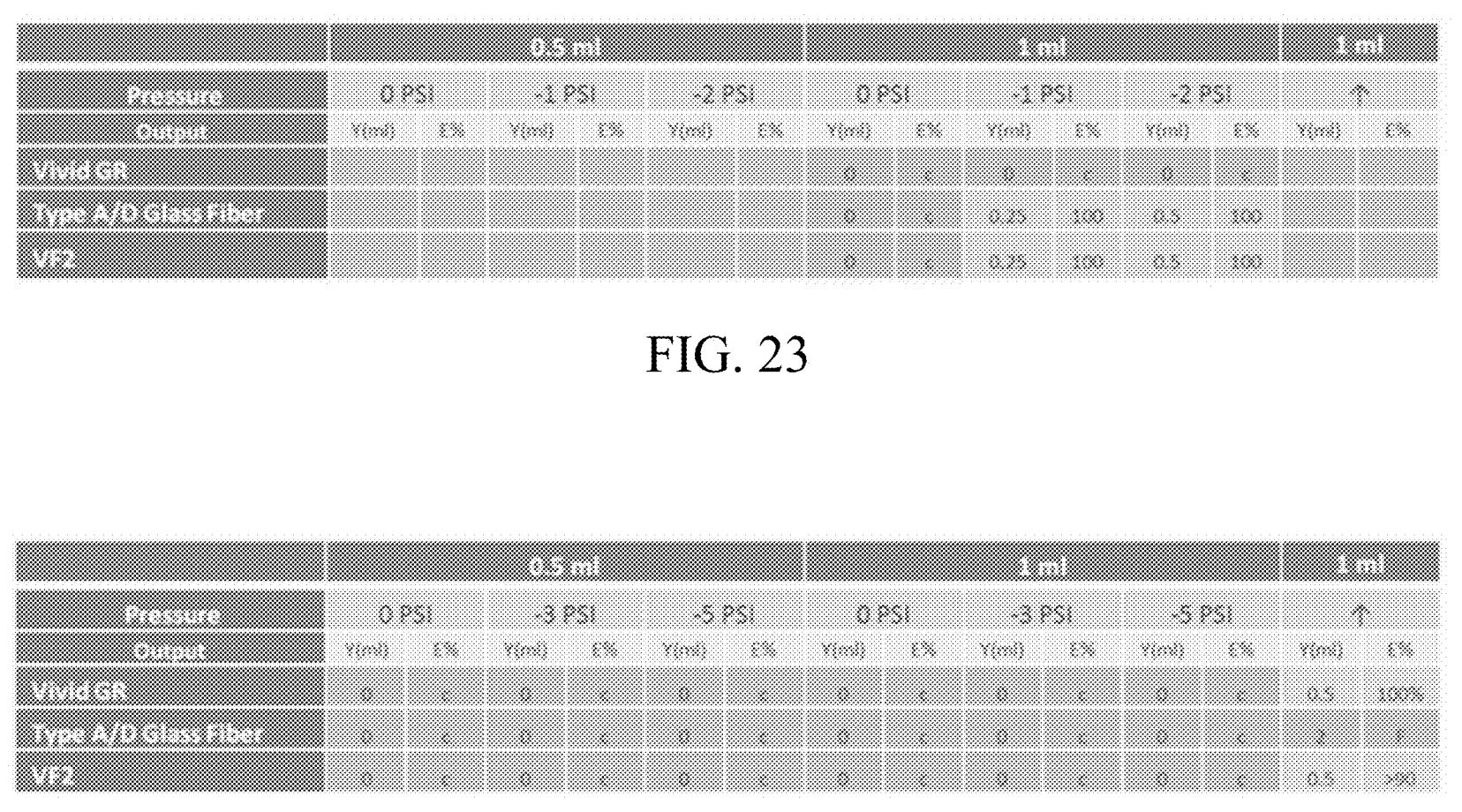

FIG. 21 depicts test results for 25 mm diameter filtration membranes tested for 5 min with 50% 3-10 um microbeads in RF. FIG. 22 depicts test results for 25 mm diameter filtration membranes tested for 5 min with 1% 10-25 um microbeads in RF. FIG. 23 depicts test results for 25 mm diameter filtration membranes tested for 5 min with 50% 3-10 um+1% 10-25 um microbeads in RF at low pressure. FIG. 24 depicts test results for 13 mm diameter filtration membranes tested for 5 min with 50% 3-10 um microbeads in RF.

Figure 25:
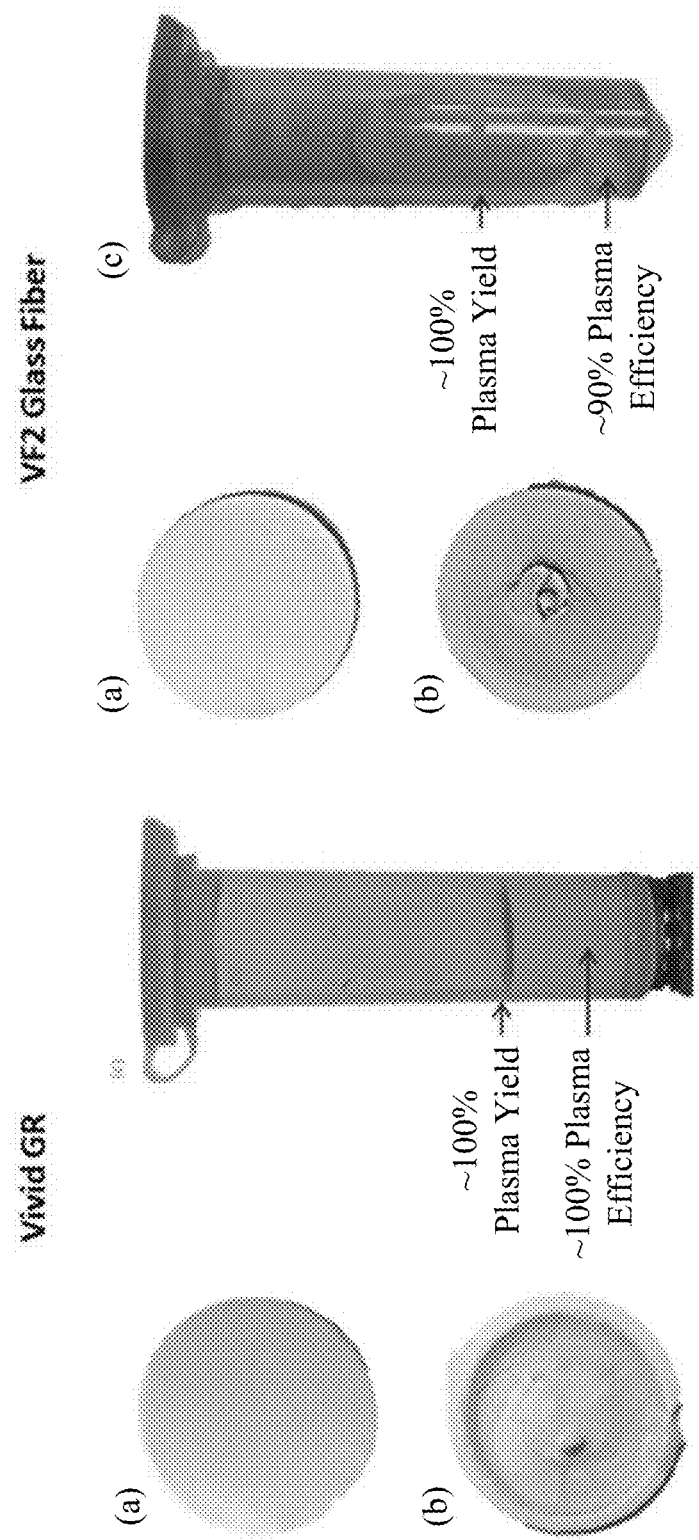
FIG. 25 are photographs of two filter assemblies.

An evaluation summary of the 6 membranes performance is provided in Table 10. Both the Vivid GR and the VF2 glass fiber membranes had ~100% yield and very high separation efficiency (see FIG. 25). FIG. 25 depicts the Vivid GR (a) membrane before filtration (b) after filtration (c)

filtered sample after centrifugation and the VF2 (a) membrane before filtration (b) after filtration (c) filtered sample after centrifugation.

Asymmetric membranes were a better choice over the symmetric membranes in dead end filtration due to having a fiber structure and void space that reduces clogging. The Vivid GR and VF2 membranes showed the best performance when tested with the blood mimicking fluid.

Example 7: Oil Pinching for Plasma Separation

Tubes received 1 mL of blood and 1 mL of mineral oil, prior to undergoing centrifugation. The oil remained on top of the blood phases in both the pre-centrifugation and post-centrifugation tubes.

Tubes were tilted in order to achieve in-oil blood separation (pinching) of the plasma within the oil. It was found that although it was not possible to obtain separation in the 15 ml centrifuge tubes due to its wider diameter compared to tubes having an 8 mm diameter. Tubes that had a diameter of 8 mm were able to be separated. See FIGS. 3A-3B.

Figure 3C:
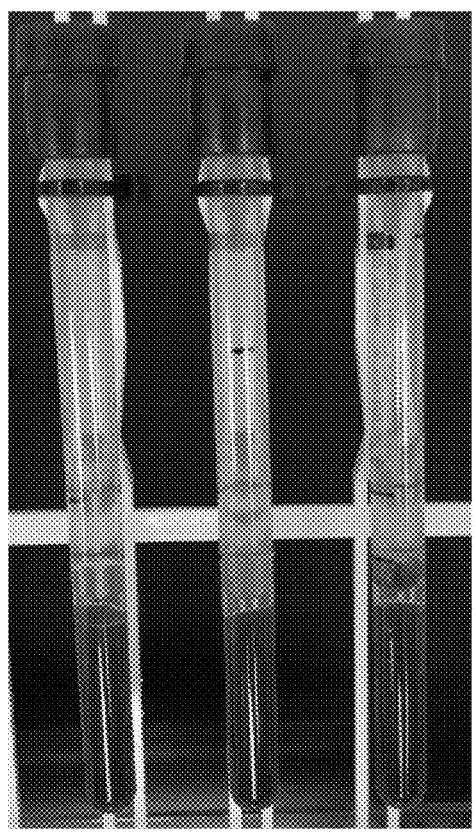

The effect of the amount of oil present in the tube was also tested. FIG. 3C shows three tubes that contained 0.5 mL, 1 mL, and 2 mL of mineral oil, from left to right. Each tube additional had 1 mL of blood, which had been separated into the blood components.

Each tube was tilted in order to create a pinch in order to separate the plasma component. The position within the tube where the pinch occurred was changed due to the amount of oil. In the left tube, the pinch occurred such that not all of the plasma was included the oil separation. In the middle tube, a there is a clear separation between the plasma, which is fully contained in the oil separation, and the remaining blood components. In the right tube, the pinch occurred such that some of the red blood cells were also caught in the oil separation, preventing a clean plasma sample. 1 mL of oil was therefore found to be the ideal amount for the tube size used in this example.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

It will be appreciated that the methods and compositions of the instant disclosure can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. An automated method to separate previously fractionated blood components, the method comprising:
   providing at least one fractionated blood sample from a sample vessel to a device comprising:
   a piercing post to receive a sample, wherein the sample vessel and the piercing post are in fluid communication, and,
   at least a first and second arm, each extending perpendicular to length of the piercing post/sample vessel complex in opposite directions, wherein each at least first and second arm has a bend at the distal end of the perpendicular segment, and a second portion of each arm which extends from the bend in a direction perpendicular to the first segment and parallel to the piercing post, such that the distal ends of the piercing post and the second portion of the arms are in opposite directions;
   capturing optical data from the at least one fractionated blood sample by a photodetector, wherein the photodetector is in communication with a processor;
   identifying a location or boundary between individual blood components in the at least one fractionated blood sample by a visual processing algorithm; and,
   providing active feedback control based on the location of or boundaries between the individual blood components as determined by the visual processing algorithm, by providing instructions to mechanical means to separate, move and store the components.

2. The method of claim 1 wherein the initial blood component fractionation is achieved by rapid sedimentation or centrifugation.

3. The method of claim 2, wherein the mechanical separation of the components by the mechanical means occurs either during or after the sedimentation process.

4. The method of claim 3, wherein the processor determines when the sedimentation process has finished.

5. The method of claim 1, wherein the processor is additionally in communication with a light source to illuminate the sample to aid in capturing optical data by a photodetector.

6. The method of claim 1, wherein valves separate the piercing post from each arm.

7. The method of claim 6, wherein each valve is independently operable.

8. The method of claim 1, wherein the device can be freely rotated.

9. A device for handling components of a biological sample, wherein the device comprises a sample vessel and a piercing post to receive a sample, such that the sample vessel and the piercing post are in fluid communication, and the piercing post comprises at least a first and second arm extending perpendicular to a length of the sample vessel, wherein,
   each of the first and second arms are arranged in opposite direction to each other, wherein each at least first and second arm has an "L" shape, such that each at least first and second arm has a first perpendicular segment, wherein a proximal end of the first perpendicular segment is attached to the piercing post, and a distal end of the first perpendicular segment has a bend between the first perpendicular segment, and a second portion of each arm, wherein the second portion extends from the bend in a direction perpendicular to the first segment and parallel to the piercing post, such that the distal ends of the piercing post and the second portion of the arms are in opposite directions.

10. The device of claim 9, wherein valves separate the piercing post from each arm.

11. The device of claim 9, wherein each valve is independently operable.

* * * * *